United States Patent
Wang et al.

(10) Patent No.: US 9,790,266 B2
(45) Date of Patent: Oct. 17, 2017

(54) GROWTH HORMONE SECRETAGOGUE RECEPTOR BASED PROTEIN

(71) Applicant: Qinghua Wang, North York (CA)

(72) Inventors: Qinghua Wang, North York (CA); Younes Anini, Halifax (CA)

(73) Assignee: Qinghua Wang, North York, Ontario (CA)

( * ) Notice: Subject to any disclaimer, the term of this patent is extended or adjusted under 35 U.S.C. 154(b) by 0 days.

(21) Appl. No.: 14/776,318

(22) PCT Filed: Mar. 14, 2014

(86) PCT No.: PCT/CA2014/000271
§ 371 (c)(1),
(2) Date: Sep. 14, 2015

(87) PCT Pub. No.: WO2014/138937
PCT Pub. Date: Sep. 18, 2014

(65) Prior Publication Data
US 2016/0130322 A1   May 12, 2016

Related U.S. Application Data

(60) Provisional application No. 61/784,267, filed on Mar. 14, 2013.

(51) Int. Cl.
C07K 14/72 (2006.01)
A61K 48/00 (2006.01)

(52) U.S. Cl.
CPC ............ *C07K 14/723* (2013.01); *A61K 48/00* (2013.01); *C07K 14/72* (2013.01); *C07K 2319/30* (2013.01); *C07K 2319/32* (2013.01)

(58) Field of Classification Search
None
See application file for complete search history.

(56) References Cited

FOREIGN PATENT DOCUMENTS

| WO | 00/77191 A1 | 12/2000 | |
|---|---|---|---|
| WO | 2007/101021 A2 | 9/2007 | |
| WO | 2008/143910 A2 | 11/2008 | |
| WO | WO2008143910 | * 11/2008 | ........... C07K 14/705 |

OTHER PUBLICATIONS

PubMed search for GHR1a—Nov. 20, 2016.*
Ueda et al., Mutational analysis of predicted extracellular domains of human growth hormone secretagogue receptor 1a. Reg. Peptides 166, 28-35, 2011.*
Beck A. and Reichert JM. Therapeutic Fc-fusion proteins and peptides as successful alternatives to antibodies. mAbs Sep./Oct. 2011, vol. 3, pp. 415-416.
Gagnon J. Unravelling the Mechanism of Ghrelin Secretion and the Effects of Ghrelin Reduction Using a Receptor Decoy Approach. PhD thesis (Dalhousie University), Chapter 6, pp. 133-157, Mar. 18, 2013. Retrieved from the Internet: <http://dalspace.library.dal.ca/handle/10222/21435>.
Pedretti, A. et al. Construction of Human Ghrelin Receptor (hGHS-R1a) Model Using a Fragmental Prediction Approach and Validation through Docking Analysis. J. Med. Chem. Jun. 2006, vol. 49, No. 11, pp. 3077-3085.
Rodriguez, A. et al. Acylated and desacyl ghrelin stimulate lipid accumulation in human visceral adipocytes. Int. J. Obes (Lond.), May 2009, vol. 33, No. 5, pp. 541-552.
Wortley, K. E. et al. Genetic deletion of ghrelin does not decrease food intake but influences metabolic fuel preference. Proc. Natl. Acad. Sci. USA. May 25, 2004, vol. 101, No. 21, pp. 8227-8232.
Zorrilla, E. P. et al. Vaccination against weight gain. Proc. Natl. Acad. Sci. USA. Aug. 29, 2006, vol. 103, No. 35, pp. 13226-13231.
Tschop, M. et al. Ghrelin induces adiposity in rodents. Nature, 407(6806), pp. 908-913.
Zhu X. et al. On the processing of proghrelin to ghrelin. J. Biol. Chem, Dec. 15, 2006, vol. 281, No. 50, pp. 38867-38870.
Zigman, J. M., Mice lacking ghrelin receptors resist the development of diet-induced obesity. J. Clin. Invest. Dec. 2005, vol. 115, No. 12, pp. 3564-3572.
Ariyasu et al. Stomach Is a Major Source of Circulating Ghrelin, and Feeding State Determines Plasma Ghrelin-Like Immunoreactivity Levels in Humans. J. Clin. Endocrinol. Metab. Oct. 2001, 86(10), pp. 4753-4758.
Banks, W. A., et al. Extent and direction of ghrelin transport across the blood-brain barrier is determined by its unique primary structure. J. Pharmacol. Exp. Ther. Aug. 2002, vol. 302, No. 2, pp. 822-827.
Broglio, F. et al. Ghrelin, a natural GH secretagogue produced by the stomach, induces hyperglycemia and reduces insulin secretion in humans. J. Clin. Endocrinal. Metab. Oct. 2001, vol. 86, No. 10, pp. 5083-5086.
Cowley M. A., et al. The distribution and mechanism of action of ghrelin in the CNS demonstrates a novel hypothalamic circuit regulating energy homeostasis. Neuron, Feb. 20, 2003, vol. 37, No. 4, pp. 649-661.

(Continued)

*Primary Examiner* — Elly-Gerald Stoica
(74) *Attorney, Agent, or Firm* — Bereskin & Parr LLP; Carmela De Luca

(57) ABSTRACT

Ghrelin is a peptide hormone that binds its receptor, growth hormone secretatgogue receptor 1a (GHS-R1 a, ghrelin receptor), to promote adiposity and obesity in mammals. Ghrelin and its receptor are targets for therapeutic intervention to treat obesity-related disease and cancer. A soluble decoy GHS-R1 a receptor is developed that binds ghrelin in the periphery, preventing ghrelin from binding GHS-R1 on cells, thereby antagonizing ghrelin to treat obesity-related pathological conditions and cancer. GHS-R1 a is a transmembrane protein comprising an N-terminal extracellular domain (Nt), seven transmembrane regions and three extracellular loops (EC1, EC2 and EC3). The Nt, EC1 and EC2 are linked together, in the absence of the transmembrane regions, and fused to a Fc from an immunoglobulin, to create the decoy GHS-R1 a fusion protein, GHSR-Fc. The GHSR-Fc inhibits adiposity and weight gain in mice on a high fat diet (HFD), while the Nt and ECs on their own have no significant effect.

10 Claims, 5 Drawing Sheets

(56) References Cited

OTHER PUBLICATIONS

Davies, J. S., et al. Ghrelin induces abdominal obesity via GHS-R-dependent lipid retention. Mol. Endocrinol. Jun. 2009. vol. 23, No. 6, pp. 914-924.
Gauna C. et al. Ghrelin stimulates, whereas des-octanoyl ghrelin inhibits, glucose output by primary hepatocytes. J. Clin. Endocrinol Metab. Feb. 2005, vol. 90, No. 2, pp. 1055-1060.
Nakazato M. et al. A role for ghrelin in the central regulation of feeding. Nature. Jan. 2001, vol. 409, No. 6817, pp. 194-198.

\* cited by examiner

GROWTH HORMONE SECRETAGOGUE RECEPTOR BASED PROTEIN

RELATED APPLICATIONS

This application is a National Stage entry of International Application No. PCT/CA2014/000271, filed Mar. 14, 2014 and claims the benefit of U.S.C. §119 based on the priority of U.S. Provisional Patent Application No. 61/784,267 filed Mar. 14, 2013, which is incorporated herein by reference in its entirety.

INCORPORATION OF SEQUENCE LISTING

A computer readable form of the Sequence Listing "P43662US01_RevisedSL.txt" (19,024 bytes), submitted via EFS-WEB and created on Dec. 29, 2015, is herein incorporated by reference.

Please replace any Sequence Listing currently of record with the Sequence Listing provided herewith in text format in computer readable form only.

FIELD

The present disclosure relates to compositions and methods useful in reducing excessive adiposity and treating or preventing obesity and obesity-related conditions.

BACKGROUND

Excessive adiposity is a risk factor for many chronic diseases, including type 2 diabetes mellitus (T2DM), cardiovascular disease, and cancer (Wang, McPherson et al. 2011). Studies have shown that even a modest reduction in weight has a positive impact on cardiovascular risk factors (Blackburn 1995; Pi-Sunyer 1996) and is associated with a reduced risk for both developing T2DM and diabetes-associated complications (Bosello, Armellini et al. 1997).

Lifestyle interventions aimed at reducing calories and increasing physical activity through behavioral changes are currently recommended as the first-line approach for weight management. However, these strategies alone are less successful when compared to pharmacological interventions for maintained weight loss (6 to 12 months) (Gray, Cooper et al. 2012). Unfortunately, most of the drugs approved for the treatment of obesity have been withdrawn from use due to their side effects (Gray, Cooper et al. 2012). Recently, targeting of gut hormones for the treatment of obesity has garnered interest (Neary and Batterham 2009). Indeed, infusion of glucagon-like peptide 1 (GLP-1) and peptide YY (PYY) are able to reduce appetite by acting on feeding regions of the brain in humans (De Silva, Salem et al. 2011). Another promising candidate is the stomach-derived peptide hormone ghrelin. Ghrelin levels peak in circulation during energy depleted states leading to activation of the appetite stimulating neuropeptide Y (NPY) and Agouti gene-related peptide (AgRP) neurons within the arcuate nucleus of the hypothalamus (Nakazato, Murakami et al. 2001). This action occurs via ghrelin binding to the growth hormone secretagogue receptor (GHS-R1a) (Kamegai, Tamura et al. 2000). In addition to appetite, ghrelin promotes the differentiation of adipocytes and the preference for storage of calories in adipose tissue (Tschop, Smiley et al. 2000; Rodriguez, Gomez-Ambrosi et al. 2009).

The ghrelin peptide is derived from proghrelin, which is a precursor peptide proteolytically cleaved to produce acylated ghrelin (AG) (Zhu, Cao et al. 2006), unacylated ghrelin (UAG) (Zhu, Cao et al. 2006) and obestatin (Zhang, Ren et al. 2005). However, in vitro studies have shown that both UAG (Kojima, Hosoda et al. 1999) and obestatin (Zhang, Ren et al. 2005) are unable to bind to GHS-R1a. The GHS-R1a is a G-protein-coupled receptor (Howard, Feighner et al. 1996), and is activated through the binding of its only known endogenous ligand, AG (Kojima, Hosoda et al. 1999). A recent study suggested that AG binds to GHS-R1a in the second extracellular loop (EC2), which forms a hydrophobic pocket, allowing the lipophylic acylated side chain of ghrelin to be stabilized during the binding (Pedretti, Villa et al. 2006).

SUMMARY

The present inventors have shown that in vivo expression of GHS-R1a fusion construct containing the N-terminal and extracellular binding loops 1 and 2 (GHSR/Fc) caused a reduction in AG but, interestingly, not UAG levels, and protected mice from high fat diet induced weight gain, which was associated with altered adipose gene expression profile and improved glucose clearance and insulin sensitivity. These observations suggest that the GHSR/Fc fusion construct may find clinical use in treating obesity and obesity-related conditions.

Accordingly, in one aspect, the present disclosure provides a soluble fusion molecule comprising (a) at least one of i) the N-terminal, ii) extracellular loop 1 and ii) extracellular loop 2, of the growth hormone secretagogue receptor (GHS-R1a); linked to (b) a fusion partner.

In an embodiment, the soluble fusion molecule comprises at least two of i) the N-terminal, ii) the extracellular loop 1 and ii) the extracellular loop 2 of the GHS-R1a, linked to a fusion partner. In another embodiment, the soluble fusion molecule comprises i) the N-terminal, ii) the extracellular loop 1 and iii) the extracellular loop 2 of the GHS-R1a, linked to a fusion partner. In yet a further embodiment, the soluble fusion molecule consists of i) the N-terminal, ii) the extracellular loop 1 and iii) the extracellular loop 2 of the GHS-R1a, linked to a fusion partner.

In one embodiment, the N-terminal region of the GHS-R1a has the amino acid sequence as shown in SEQ ID NO:4 or 13 or a variant thereof; the extracellular loop 1 has the amino acid sequence as shown in SEQ ID NO:6 or 15 or a variant thereof; and/or the extracellular loop 2 has the amino acid sequence as shown in SEQ ID NO:8 or 17 or a variant thereof.

In another embodiment, the N-terminal region of the GHS-R1a is encoded by the nucleic acid sequence as shown in SEQ ID NO:3 or 12 or a variant thereof; the extracellular loop 1 is encoded by the nucleic acid sequence as shown in SEQ ID NO:5 or 14 or a variant thereof; and/or the extracellular loop 2 is encoded by the nucleic acid sequence as shown in SEQ ID NO:7 or 16 or a variant thereof.

In an embodiment, the fusion partner is a stabilizing molecule, such as a stabilizing protein or a polymer. In one embodiment, the stabilizing protein is an immunoglobulin constant region (Fc) or an albumin protein. In an embodiment, the Fc region is an IgG Fc region, optionally IgG2 or IgG4. In another embodiment, the stabilizing polymer is a polyethylene glycol.

The soluble fusion molecule of the present disclosure can be linked directly or can comprise a peptide linker between more than one extracellular GHS-R1a domain and/or between the GHS-R1a extracellular domain(s) and the fusion partner.

In one embodiment, the soluble fusion molecule has the amino acid sequence as shown in SEQ ID NO:2 or 11 or a variant thereof or is encoded by the nucleic acid sequence as shown in SEQ ID NO:1 or 10 or a variant thereof.

Also provided herein is a nucleic acid molecule encoding a soluble fusion molecule of the present disclosure, wherein a) and b) are proteins, optionally linked by a peptide linker.

In another embodiment, the present disclosure provides an isolated nucleic acid molecule encoding the N-terminal domain of GHS-R1a. In one embodiment, the isolated nucleic acid comprises the nucleic acid sequence as shown in SEQ ID NO:3 or 12 or encodes the amino acid sequence as shown in SEQ ID NO:4 or 13. In another embodiment, the present disclosure provides an isolated nucleic acid molecule encoding the extracellular loop 1 of GHS-R1a. In one embodiment, the isolated nucleic acid comprises the nucleic acid sequence as shown in SEQ ID NO:5 or 14 or a variant thereof or encodes the amino acid sequence as shown in SEQ ID NO:6 or 15 or a variant thereof. Further provided herein is an isolated nucleic acid molecule encoding the extracellular loop 2 of GHS-R1a. In one embodiment, the isolated nucleic acid comprises the nucleic acid sequence as shown in SEQ ID NO:7 or 16 or a variant thereof or encodes the amino acid sequence as shown in SEQ ID NO:8 or 17 or a variant thereof.

Also provided is a host cell comprising a nucleic acid molecule of the disclosure.

Even further provided is a composition, optionally a pharmaceutical composition comprising a soluble fusion molecule of the present disclosure, a nucleic acid molecule of the present disclosure, a host cell of the present disclosure, or an extracellular domain of the growth hormone secretagogue receptor (GHS-R1a), and a carrier optionally a pharmaceutically acceptable carrier. In an embodiment, the GHS-R1a extracellular domain is selected from the N-terminal region, the extracellular loop 1 and/or the extracellular loop 2 or a combination thereof. In another embodiment, the GHS-R1a extracellular domain is the extracellular loop 1 and/or 2.

In another aspect, the present disclosure provides a method of reducing excessive adiposity in an animal comprising administering a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for reducing excessive adiposity in an animal in need thereof. Further provided is a use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) in the manufacture of a medicament for reducing excessive adiposity in an animal in need thereof. Even further provided is a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for use in reducing excessive adiposity in an animal in need thereof. In an embodiment, the GHS-R1a extracellular domain is selected from the N-terminal region, the extracellular loop 1 and/or the extracellular loop 2 or a combination thereof. In another embodiment, the GHS-R1a extracellular domain is the extracellular loop 2.

In one embodiment, the present disclosure provide a method of reducing weight gain in an animal comprising administering a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) to the animal in need thereof. Also provided is use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for reducing weight gain in an animal in need thereof. Further provided is use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) in the manufacture of a medicament for reducing weight gain in an animal in need thereof. Even further provided is a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for use in reducing weight gain in an animal in need thereof. In an embodiment, the GHS-R1a extracellular domain is selected from the N-terminal region, the extracellular loop 1 and/or the extracellular loop 2 or a combination thereof. In another embodiment, the GHS-R1a extracellular domain is the extracellular loop 2.

In another embodiment, the present disclosure provides a method of treating obesity or an obesity-related condition in an animal comprising administering a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for treating obesity or an obesity-related condition in an animal in need thereof. Further provided is a use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) in the manufacture of a medicament for treating obesity or an obesity-related condition in an animal in need thereof. Even further provided is a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for use in treating obesity or an obesity-related condition in an animal in need thereof. In an embodiment, the GHS-R1a extracellular domain is selected from the N-terminal region, the extracellular loop 1 and/or the extracellular loop 2 or a combination thereof. In another embodiment, the GHS-R1a extracellular domain is the extracellular loop 2.

In one embodiment, the obesity-related condition is type 2 diabetes, cardiovascular disease or cancer. Among the types of cancer most strongly linked to obesity are esophagus, breast, endometrium, colorectal and pancreas. Accordingly, in an embodiment, the cancer is cancer of the esophagus, breast, endometrium, colorectal and pancreas. In another embodiment, the obesity-related condition is high cholesterol, high triglycerides, high blood pressure metabolic syndrome (a combination of high blood sugar, high blood pressure, high triglycerides and high cholesterol) or polycystic ovarian syndrome (PCOS).

In yet a further embodiment, the present disclosure provides a method of improving glucose tolerance and/or insulin sensitivity in an animal comprising administering a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for improving glucose tolerance and/or insulin sensitivity in an animal in need thereof. Further provided is use of a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) in the manufacture of a medicament for improving glucose tolerance and/or insulin sensitivity in an animal in need thereof. Even further provided is a soluble fusion molecule of the present disclosure, a nucleic acid molecule of the present disclosure, a host cell of the present disclosure, a pharmaceutical composition of the present disclosure or an extracellular domain of the growth hormone secretagogue receptor (GHS-R1a) for use in improving glucose tolerance and/or insulin sensitivity in an animal in need thereof. In an embodiment, the GHS-R1a extracellular domain is selected from the N-terminal region, the extracellular loop 1 and/or the extracellular loop 2 or a combination thereof. In another embodiment, the GHS-R1a extracellular domain is the extracellular loop 2.

The animal may be any animal, optionally humans. In one embodiment, the animal has Type 2 diabetes.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

The present inventors developed GHS-R1a-fusion constructs of a decoy protein containing the ligand-binding domains of the ghrelin receptor. Intramuscular injection of the GHSR/Fc plasmid decreased circulating levels of acylated-ghrelin. Upon challenge with high fat diet (HFD), treated mice displayed reduced weight gain compared to controls, which is associated with reduced fat accumulation in the peritoneum but not lean mass. Quantitative RT-PCR showed increased PPARγ and hormone sensitive lipase transcripts levels in adipose tissue of treated animals, illustrating a preference for increased fat utilization. Intraperitoneal glucose tolerance and insulin tolerance tests showed improved glucose clearance and insulin sensitivity in GHSR/Fc-treated animals. Thus, in vivo expression of the GHSR-based fusion protein prevents diet-induced weight gain, altering adipose gene expression and improving glucose tolerance.

The present inventors have shown that in vivo expression of GHS-R1a fusion construct containing the extracellular binding loops 1 and 2 (GHSR/Fc) caused a reduction in acylated ghrelin (AG) but, interestingly, not unacylated ghrelin (UAG) levels, and protected mice from high fat diet-induced weight gain, which was associated with altered adipose gene expression profile and improved glucose clearance and insulin sensitivity. These observations suggest that the GHSR/Fc fusion construct may find clinical use in treating obesity and obesity-related conditions.

Accordingly, in one aspect, the present disclosure provides a soluble fusion molecule comprising (a) at least one of i) the N-terminal, ii) extracellular loop 1 and iii) extracellular loop 2, of the growth hormone secretagogue receptor (GHS-R1a); linked to (b) a fusion partner.

Figure 1:
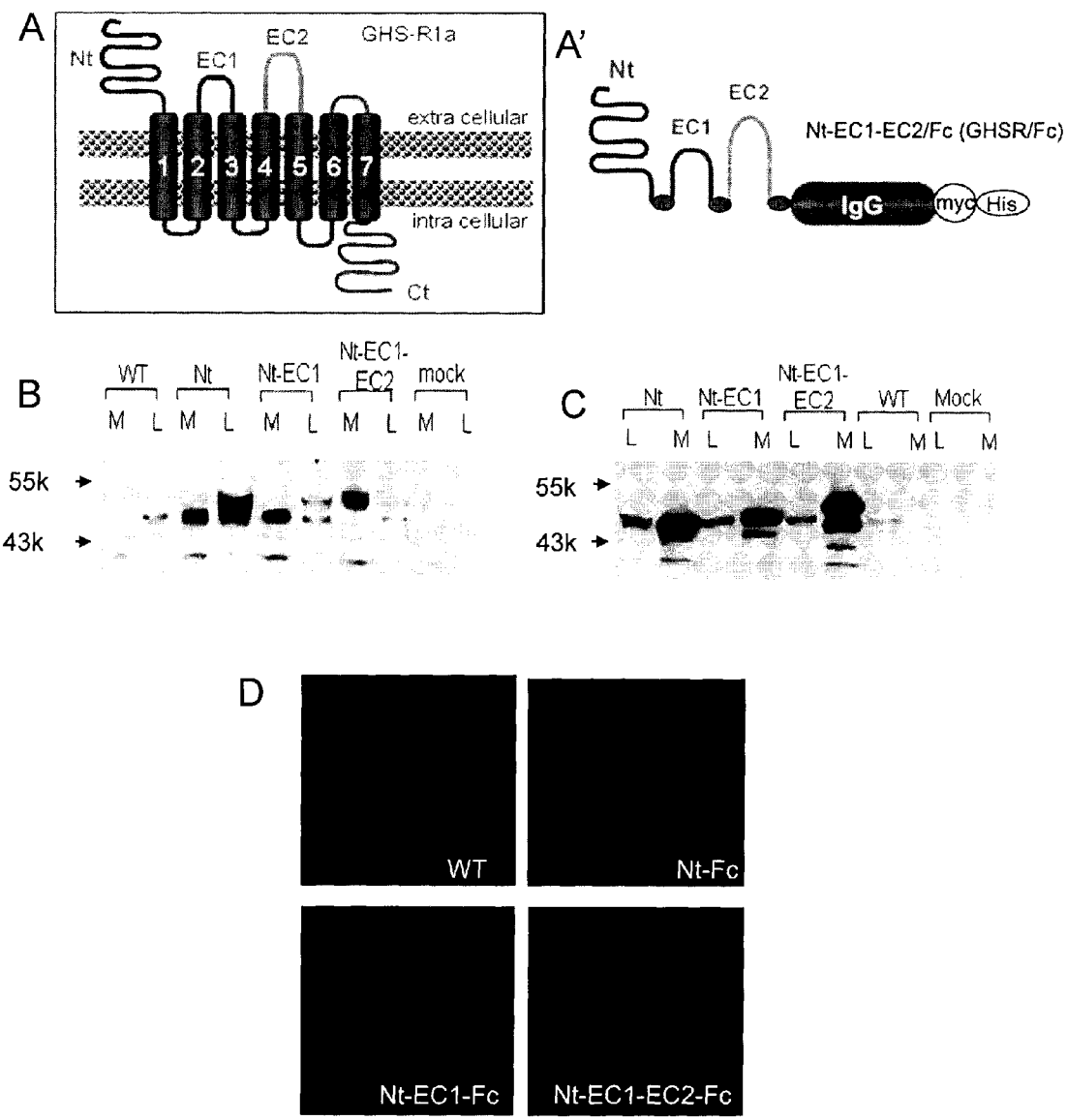
FIG. 1 shows the validation of GHSR related constructs. Illustration of the full length (WT) and extracellular domain (GHSR/Fc) constructs (A). Domains are identified as N-terminal (Nt), extracellular domain 1 and 2 (EC1, EC2) and mouse immunoglobulin IgG1 constant region (Fc). Western blots were performed using anti-Myc tag antibody for immunoblotting of cell lysates (L) and culture media (M) from L6 cells (B), and CHO (C) cells transfected with GHSR/Fc based constructs. Fluorescent immunocytochemistry using anti-mouse IgG-Fc was conducted in L6 muscle cells transfected with WT and GHSR/Fc plasmids (D, transfected cells appear gray in the Figure).

The term "growth hormone secretagogue receptor" or "GHS-R1a" refers to the full length growth hormone secretagogue receptor from any species or source, optionally mammalian, such as human or mouse and isoforms and homologs thereof. Such receptors have both extracellular and intracellular domains including when folded properly as in FIG. 1A an N-terminal domain (NTD), three extracellular loops (EC1, EC2 and EC3) and transmembrane domains. The nucleotide sequence of human GHS-R1a is as shown in SEQ ID NO: 18 and encodes the human GHS-R1a protein under Genbank Accession No. Q92847 The nucleotide sequence of murine GHS-R1a is as shown in SEQ ID NO:9 and encodes the murine GHS-R1a protein under Genbank Accession No. Q99P50.

The term "extracellular domain of GHS-R1a" refers to a domain of the GHS-R1a receptor that lacks the transmembrane and intracellular domains of the receptor, and includes, without limitation, the N-terminal domain, the extracellular loop 1 and the extracellular loop 2.

The term "N-terminal" as used herein refers to an isolated peptide corresponding to the amino acid sequence coding for the N-terminal extracellular region of GHS-R1a. In an embodiment, the N-terminal domain extends to the last amino acid of the extracellular domain preceding the transmembrane domain amino acid sequence.

The term "extracellular loop" as used herein refers to an isolated protein comprising the sequence of a portion of the GHS-R1a that forms a loop on the extracellular side of the cell membrane. GHS-R1a has a first extracellular loop from 102 to 127 amino acids of human GHS-R1a and from 101 to 126 amino acids of mouse GHS-R1a, termed extracellular loop 1, and a second extracellular loop from 182 to 207 amino acids of human GHS-R1a and from 181 to 206 amino acids of mouse GHS-R1a, termed extracellular loop 2.

In an embodiment, the fusion molecule comprises at least two of i) the N-terminal, ii) the extracellular loop 1 and ii) the extracellular loop 2 of the GHS-R1a, linked to a fusion partner. In another embodiment, the fusion molecule comprises i) the N-terminal, ii) the extracellular loop 1 and iii) the extracellular loop 2 of the GHS-R1a, linked to a fusion partner. In yet a further embodiment, the fusion molecule consists of i) the N-terminal, ii) the extracellular loop 1 and iii) the extracellular loop 2 of the GHS-R1a, linked to a fusion partner.

In one embodiment, the N-terminal region of the GHS-R1a has the amino acid sequence as shown in SEQ ID NO:4 or 13 or a variant thereof or is encoded by the nucleic acid sequence as shown in SEQ ID NO:3 or 12 or a variant thereof; the extracellular loop 1 has the amino acid sequence as shown in SEQ ID NO:6 or 15 or a variant thereof or is encoded by the nucleic acid sequence as shown in SEQ ID NO:5 or 14 or a variant thereof; and/or the extracellular loop 2 has the amino acid sequence as shown in SEQ ID NO:8 or 17 or a variant thereof or is encoded by the nucleic acid sequence as shown in SEQ ID NO:7 or 16 or a variant thereof.

The term "a fusion molecule" refers to the linking of a peptide sequence derived from the extracellular domain or domains of GHS-R1a to a fusion partner and can be a direct or indirect linkage via a covalent or non-covalent linkage.

The fusion partner may be linked to either the N-terminus or the C-terminus of the peptide sequence derived from GHS-R1a.

The term "soluble fusion molecule" as used herein refers to the fusion molecule as lacking any transmembrane or intracellular domains and if expressed from a nucleotide sequence in a cell, would be a secreted protein.

In an embodiment, the fusion partner is a stabilizing molecule, such as a stabilizing protein or a polymer.

The term "stabilizing molecule" as used herein refers to a molecule that when linked to the extracellular domain(s) provides an increased half-life and/or reduced immunogenicity compared to the extracellular domain(s) without such molecule.

In one embodiment, the stabilizing protein is an immunoglobulin constant region (Fc) or an albumin protein. In an embodiment, the Fc region is an IgG Fc domain, optionally mouse IgG1 or human IgG2 or IgG4. In another embodiment, the stabilizing polymer is a polyethylene glycol or the like.

In another embodiment, the soluble fusion molecule comprises the amino acid sequence as shown in SEQ ID NO:2 or 11 or a variant thereof or is encoded by the nucleic acid sequence as shown in SEQ ID NO:1 or 10 or a variant thereof.

The domains or regions of the soluble fusion molecule of the present disclosure can be linked directly or can comprise a linker between each region, optionally a peptide linker. The peptide linker can be any size provided it does not interfere with the function of the individual linked regions. In one embodiment, the peptide linker is from about 1 to about 15 amino acids in length, more specifically from about 1 to about 10 amino acids, and most specifically from about 1 to about 6 amino acids. Where the soluble fusion molecule is made solely of fused peptides, it may be part of a continuous sequence and as such can be translated as a single polypeptide from a coding sequence that codes for both the at least one extracellular domain and the stabilizing protein.

In other embodiments, one of skill in the art can appreciate that the fusion molecule can also be formed by linking the at least two protein regions in vitro, for example, using chemical cross-linkers.

As used herein, the term "protein" or "polypeptide" refers to a sequence of amino acid residues encoded by a nucleic acid molecule. Within the context of the present application, a polypeptide of the disclosure may in one embodiment include various structural forms of the primary protein. For example, a polypeptide of the disclosure may be in the form of acidic or basic salts or in neutral form. In addition, individual amino acid residues may be modified by oxidation or reduction.

The proteins and polypeptides of the present disclosure may also include truncations, analogs and homologs of the proteins and polypeptides as described herein having substantially the same function as the proteins or polypeptides of the present disclosure, such as the ability to decrease acylated ghrelin.

Analogs of the proteins described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the disclosure with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

Conservative substitutions are described in the patent literature, as for example, in U.S. Pat. No. 5,264,558. It is thus expected, for example, that interchange among nonpolar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. Other substitutions might well be possible.

As used herein, the term "variant thereof" means a sequence with at least 75%, 80%, 85%, 90%, 95% or 99% sequence identity to a nucleotide or amino acid sequence of interest.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can be accomplished using a mathematical algorithm. An optional, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search, which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website).

Another optional, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, the term "fragment thereof" refers to a nucleic acid or amino acid sequence comprising up to 3, 5, 10, 15, 25, 50, 100, 250, 500, 1000, 2000 or 3000 contiguous residues of a nucleotide or amino acid sequence of interest.

Within the context of the present disclosure, a protein of the disclosure may include various structural forms of the primary protein which retain biological activity. For example, a protein of the disclosure may be in the form of acidic or basic salts or in neutral form. In addition, individual amino acid residues may be modified by oxidation or reduction.

Exemplary methods of making the alterations set forth above are disclosed by Sambrook et al. (Molecular Cloning: A Laboratory Manual, 2nd Ed., Cold Spring Harbor Laboratory Press, 1989).

Also provided herein is a nucleic acid molecule encoding the soluble fusion molecule of the present disclosure, wherein the molecule optionally comprise a peptide linker joining the various domains of the fusion molecule.

In another embodiment, the present disclosure provides an isolated nucleic acid molecule encoding the N-terminal domain of GHS-R1a. In one embodiment, the isolated nucleic acid comprises the nucleic acid sequence as shown in SEQ ID NO:3 or 12 or encodes the amino acid sequence as shown in SEQ ID NO:4 or 13. In another embodiment, the present disclosure provides an isolated nucleic acid molecule encoding the extracellular loop 1 of GHS-R1a. In one embodiment, the isolated nucleic acid comprises the nucleic acid sequence as shown in SEQ ID NO:5 or 14 or a variant thereof or encodes the amino acid sequence as shown in SEQ ID NO:6 or 15 or a variant thereof. Further provided herein is an isolated nucleic acid molecule encoding the extracellular loop 2 of GHS-R1a. In one embodiment, the isolated nucleic acid comprises the nucleic acid sequence as shown in SEQ ID NO:7 or 16 or a variant thereof or encodes the amino acid sequence as shown in SEQ ID NO:8or 17 or a variant thereof.

As used herein, the term "nucleic acid molecule" means a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences, which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The disclosure also provides isolated nucleic acid sequences encoding variants of the CDR sequences and variable region sequences discussed above.

Variant nucleic acid sequences include nucleic acid sequences that hybridize to the nucleic acid sequences disclosed herein under at least moderately stringent hybridization conditions, or have at least 50%, 60%, 70%, 80%, 90%, 95% or 98% sequence identity to the nucleic acid sequences that encode the amino acid sequences disclosed herein.

The term "sequence that hybridizes" means a nucleic acid sequence that can hybridize to a nucleic acid sequence disclosed herein under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium-containing buffers is a function of the sodium ion concentration, G/C content of labeled nucleic acid, length of nucleic acid probe (l), and temperature (Tm=81.5° C.−16.6(Log 10 [Na+])+0.41(%(G+C)−600/l). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C.

One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

A person skilled in the art will appreciate that the proteins of the disclosure may be prepared in any of several ways, including, without limitation, by using recombinant methods.

Accordingly, the nucleic acid molecules disclosed herein may be incorporated in a known manner into an appropriate expression vector which ensures good expression of the proteins. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the application and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The disclosure therefore contemplates a recombinant expression vector containing a nucleic acid molecule disclosed herein, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the disclosure may also contain a selectable marker gene which facilitates the selection of host cells transformed or transfected with a recombinant molecule of the application. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin, optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the application and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium chloride-mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the disclosure may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as Escherichia coli (Zhang et al., Science 303 (5656): 371-3 (2004)). In addition, a Pseudomonas-based expression system such as Pseudomonas fluorescens can be used (US Patent Application Publication No. US 2005/0186666, Schneider, Jane C et al.).

Accordingly, also provided herein is a host cell comprising a nucleic acid molecule of the disclosure.

Even further provided is a pharmaceutical composition comprising a soluble fusion molecule of the present disclosure, a nucleic acid molecule of the present disclosure or a host cell of the present disclosure, and a pharmaceutically acceptable carrier.

The soluble fusion molecule is optionally present in an amount effective for reducing excessive adiposity in a mammal in need thereof.

The term "effective amount" as used herein means an amount sufficient to achieve the desired result and accordingly will depend on the ingredient and its desired result. Nonetheless, once the desired effect is known, determining the effective amount is within the skill of a person skilled in the art.

Suitable pharmaceutically acceptable carriers include essentially chemically inert and nontoxic materials that do not interfere with the effectiveness of the biological activity of the pharmaceutical composition. Suitable vehicles are described, for example, in Remington's Pharmaceutical Sciences (Remington's Pharmaceutical Sciences, 20th ed., Mack Publishing Company, Easton, Pa., USA, 2000). Examples of suitable pharmaceutical carriers include, but are not limited to, water, saline solutions, glycerol solutions, ethanol, N-(1(2,3-dioleyloxy)propyl)N,N, N-trimethylammonium chloride (DOTMA), diolesylphosphotidyl-ethanolamine (DOPE), and liposomes. Such compositions contain a therapeutically effective amount of the agent, together with a suitable amount of carrier so as to provide the form for direct administration to the patient.

In some embodiments, the composition is formulated for administration to a subject such as a human. In particular embodiments, the composition is formulated for intravenous or oral administration. Optionally, the composition is formulated for inhalative, rectal or parenteral administration, including dermal, intradermal, intragastral, intracutan, intravasal, intravenous, intramuscular, intraperitoneal, intranasal, intravaginal, intrabuccal, percutaneous, subcutaneous, sublingual, topical or transdermal administration.

In another aspect, the present disclosure provides a method of reducing excessive adiposity in an animal comprising administering a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for reducing excessive adiposity in an animal in need thereof. Further provided is a use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) in the manufacture of a medicament for reducing excessive adiposity in an animal in need thereof. Even further provided is a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for use in reducing excessive adiposity in an animal in need thereof.

The phrase "reducing excessive adiposity" as used herein refers to a reduction of at least 1%, 2%, 5%, 10%, 15%, 20% or more in the amount of fat tissue in a treated subject compared to a control that is on the same or similar diet.

In one embodiment, the present disclosure provide a method of reducing weight gain in an animal comprising administering a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) to the animal in need thereof. Also provided is use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for reducing weight gain in an animal in need thereof. Further provided is use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) in the manufacture of a medicament for reducing weight gain in an animal in need thereof. Even further provided is a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for use in reducing weight gain in an animal in need thereof.

The phrase "reducing weight gain" as used herein refers to a reduction of at least 1%, 2%, 5%, 10%, 15%, 20% or more in the mass of a treated subject compared to a control that is on the same or similar diet.

In another embodiment, the present disclosure provides a method of treating obesity or an obesity-related condition in an animal comprising administering a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for treating obesity or an obesity related condition to an animal in need thereof. Further provided is a use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) in the manufacture of a medicament for treating obesity or an obesity related condition to an animal in need thereof. Even further provided is a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for use in treating obesity or an obesity related condition to an animal in need thereof.

The term "obesity" as used herein refers to a condition in a subject having an accumulation of body fat and includes, without limitation, pre-obesity typically defined as having a body mass index greater than 25, and obesity typically defined having a body mass index greater than 30 (often called obese).

The phrase "treating obesity" includes a reduction of at least 5%, 10%, 15%, 20% or more in weight compared to a non-treated subject on a similar or same diet regimen or a reduction of 5%, 10%, 15%, 20% or more in the ratio of fat mass to lean mass of the subject.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, prevention of disease spread, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. Treatment methods comprise administering to a subject a therapeutically effective amount of an active agent and optionally consists of a single administration, or alternatively comprises a series of applications. The length of the treatment period depends on a variety of factors, such as the severity of the condition, the age of the patient, the concentration of active ingredient or agent, the activity of the compositions described herein, and/or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

In one embodiment, the obesity-related condition is type 2 diabetes, cardiovascular disease or cancer. In an embodiment, the cancer is cancer of the esophagus, breast, endometrium, colorectal or pancreas.

In another embodiment, the obesity-related condition is high cholesterol, high triglycerides, high blood pressure metabolic syndrome (a combination of high blood sugar, high blood pressure, high triglycerides and high cholesterol) or polycystic ovarian syndrome (PCOS).

In yet a further embodiment, the present disclosure provides a method of improving glucose tolerance and/or insulin sensitivity in an animal comprising administering a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) to the animal in need thereof. Also provided is a use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for improving glucose tolerance and/or insulin sensitivity in an animal in need thereof. Further provided is use of a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) in the manufacture of a medicament for improving glucose tolerance and/or insulin sensitivity. Even further provided is a soluble fusion molecule of the present disclosure, a nucleic acid molecule of the present disclosure, a host cell of the present disclosure, a pharmaceutical composition of the present disclosure, or an extracellular domain of the growth hormone secretagogue receptor (GHS-R1a) for use in improving glucose tolerance and/or insulin sensitivity in an animal in need thereof.

The phrase "improving glucose tolerance and/or insulin sensitivity" as used herein refers to an improved metabolic status including reduced blood glucose levels as a result of enhanced insulin secretion and insulin action in the body. This is also exemplified by enhanced glucose uptake or utilization in the insulin-responsible tissues such as muscle, fat and liver.

The term "subject" or "animal" as used herein includes all members of the animal kingdom, including mammals, and suitably refers to humans. In one embodiment, the animal has Type 2 diabetes.

The term "administering the proteins disclosed herein" includes both the administration of protein as well as the administration of a nucleic acid sequence encoding the protein to an animal or to a cell in vitro or in vivo. The term "administering" also includes the administration of a cell that expresses the antibody or antibody fragment thereof.

The term "a cell" includes a single cell as well as a plurality or population of cells. Administering to a cell includes administering in vitro (or ex vivo) as well as in vivo.

The active agents or compositions of the present disclosure may be used alone or in combination with other known agents useful for reducing excessive adiposity or weight gain, for example, for treating obesity or an obesity-related condition in a subject. When used in combination with other agents, it is an embodiment that the compositions or active agents of the present disclosure are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present disclosure that the composition or active agent of the present disclosure and the other agent(s) is administered to a subject in a non-contemporaneous fashion.

The dosage of compositions or active agents of the present disclosure can vary depending on many factors such as the pharmacodynamic properties of the composition, the mode of administration, the age, health and weight of the recipient, the nature and extent of the symptoms, the frequency of the treatment and the type of concurrent treatment, if any, and the clearance rate of the composition in the subject to be treated. One of skill in the art can determine the appropriate dosage based on, for example the above factors. Compositions of the present disclosure may be administered initially in a suitable dosage that may be adjusted as required, depending on the clinical response, and may be administered in a single daily dose or the total daily dose may be divided into two, three or four daily doses.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Depleting circulating ghrelin holds the potential to reduce caloric intake and promote fat energy utilization. As such, mammalian expression plasmid vectors encoding the ligand binding domains of the GHS-R1a were constructed, specifically the N-terminal (Nt), and/or the first, second extracellular domain (EC1, EC2) and were fused with a mouse IgG constant regions (Fc), forming GHSR/Fc (FIG. 1A). In vivo expression of these fusion proteins was achieved through plasmid-intramuscular injection and subsequent electroporation in gastrocnemius muscle of mice. The fusion constructs omitted the sequence motif corresponding to the transmembrane domains of the receptor, allowing the production of GHSR/Fc that is secretable.

Results

Validation of GHSR Constructs

The expression and secretion of the fusion proteins were first examined under in vitro conditions by the transient transfection of the plasmid vectors (FIG. 1A) into L6 rat skeletal muscle cell line. At 48 h after transfection, the medium and the cells were harvested separately and extracted proteins were subjected to Western blot analysis using anti-Myc tag antibodies. As shown, the expression of the fusion constructs (Nt-, Nt-EC1, and Nt-EC1-EC2, denoted as GHSR/Fc) was consistently detected in both the cell lysate and culture media whereas the WT/Fc, which contains the transmembrane domains, was only found in the cell lysate (45 kD) (FIG. 1B). Similar results were also obtained in the culture media or cell lysate in CHO cells transfected with the fusion constructs (FIG. 1C). Immunocytochemistry experiments using anti IgG-Fc antibodies showed that Nt-EC1-EC2 (GHSR/Fc), Nt/Fc, EC1/Fc, and WT/Fc were detected in the transfected L6 cells (FIG. 1D), suggesting that these fusion proteins can be produced in the mammalian expression system in vitro.

Effects of In Vivo Expression of GHSR/Fc in Mice

Figure 2:
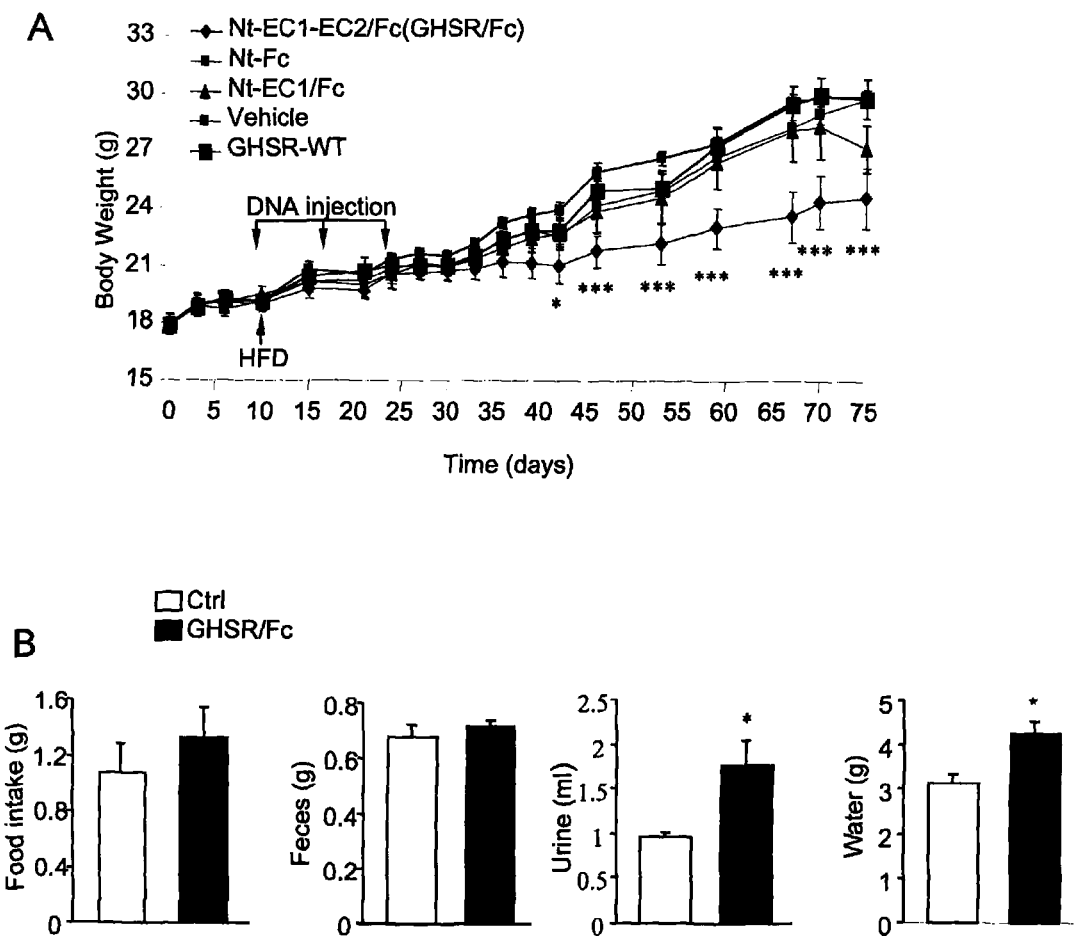
FIG. 2 shows the effect of GHSR/Fc on weight gain and metabolic parameters. Mice received three intramuscular injections of indicated plasmids, and were placed on a high fat diet (HFD) the second day after the first gene transfer. The body weight was monitored during the feeding course (A).

To examine the impact of GHSR gene therapy on energy intake and weight gain, food consumption and body weight was measured in mice injected with the GHSR-based constructs and control mice (injected with the Fc empty vector) fed on a high fat diet (HFD). Mice treated with the GHSR/Fc construct gained significantly less body weight compared to the control animals (FIG. 2A). The weight differences began at 30 days post injection ($21.0 \pm 0.195$ g vs $23.8 \pm 0.433$ g in control, $p<0.05$), and continued until the termination of the experiment at 54 days post the first injection ($23.5 \pm 1.36$ g vs $29.6 \pm 0.434$ g in control, $p<0.001$), (FIG. 2A). Mice that received Nt/Fc, Nt-EC1/Fc, or WT/Fc injections all showed a modest reduction in weight gain that did not reach statistical significance. The GHSR/Fc having the N-terminal as well as both extracellular loop 1 and extracellular loop 2 were the focus of the remaining analysis.

Since ghrelin was previously shown to have a potent orexigenic effect, the daily food and water consumption was examined. As shown in FIG. 2B, there was no difference in food intake between control and GHSR/Fc treated mice. However, treatment with GHSR/Fc increased water intake and urine.

Figure 3:
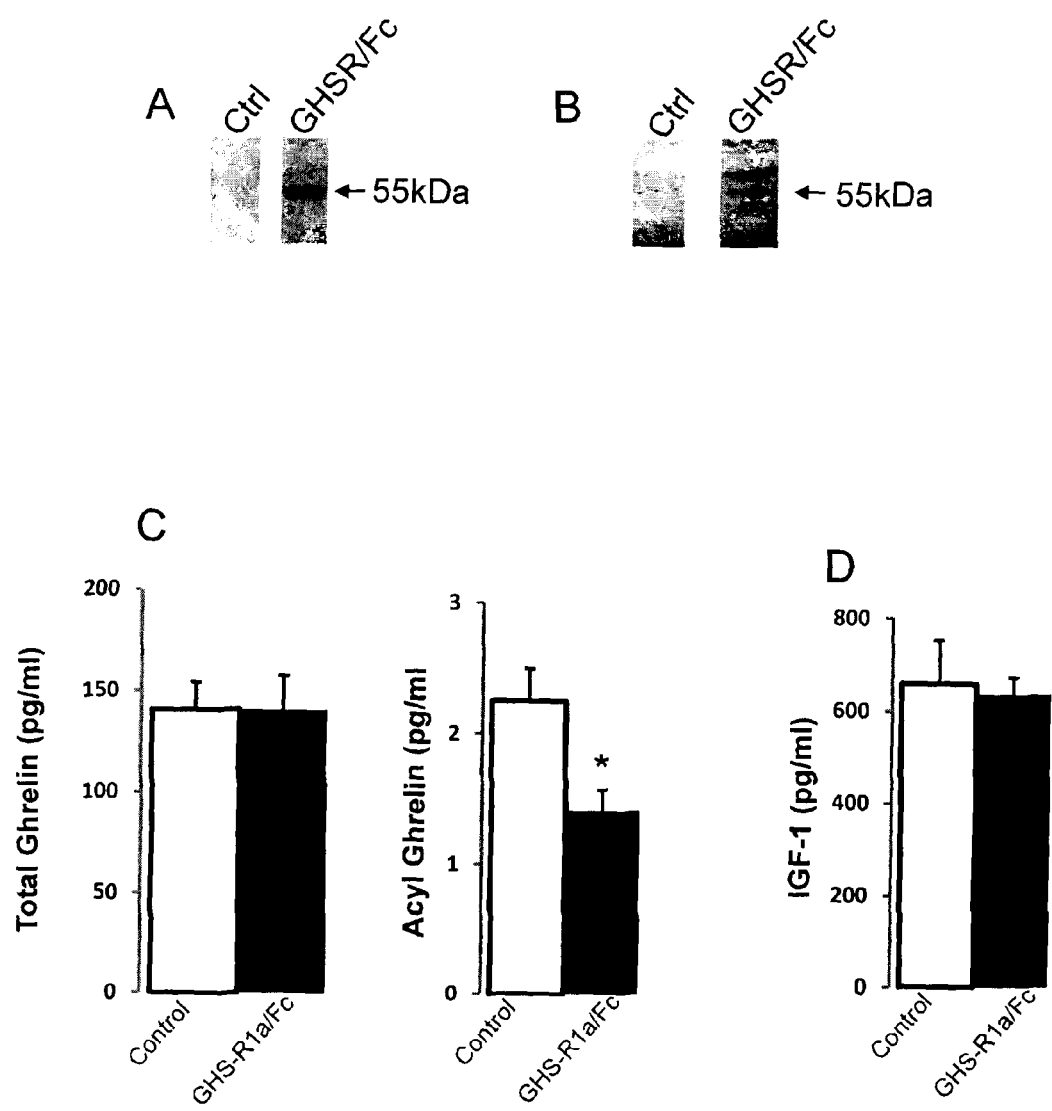
FIG. 3 shows western blots performed using anti-Myc tag antibody for immunoblotting gastrocnemius muscle tissue lysate (A) and blood plasma (B) at the end of the study. Circulating levels of total (AG and UAG), acyl specific (AG) (C) and IGF-1 (D) were assayed at the end of the study. Data are Mean±SEM, *$P<0.05$.

In vivo expression of the GHSR/Fc was verified by western blot analysis. As shown, western blotting of whole gastrocnemius muscle lysates detected a 55 kDa band corresponding to the GHSR/Fc fusion protein in each of the GHSR/Fc-treated mice (FIG. 3A). Furthermore, Western blot analysis of plasma showed the presence of the 55 kDa band in GHSR/Fc treated mice but not in vehicle-injected control mice (FIG. 3B). To confirm the ghrelin neutralizing effect of this treatment, the levels of AG and total ghrelin (primarily UAG) were measured in circulation. As shown in FIG. 3C, expression of GHSR/Fc did not alter the levels of total ghrelin (FIG. 2D 140.9±30.2 pg/ml vs 140.8±37.94 pg/ml in control) but significantly reduced the levels of AG (FIG. 2D, 1.41±0.160 pg/ml vs 2.25±0.240 pg/ml in control, $p<0.05$). Finally, to address if reduced AG levels had an effect on the growth hormone pathway, plasma levels of the GH-dependent insulin-like growth factor-1(IGF-1) were examined. No difference was found for IGF-1 levels between the GHSR/Fc treated and control mice (FIG. 3D).

Effects of GHSR/Fc on Adipose Tissue

Figure 4:
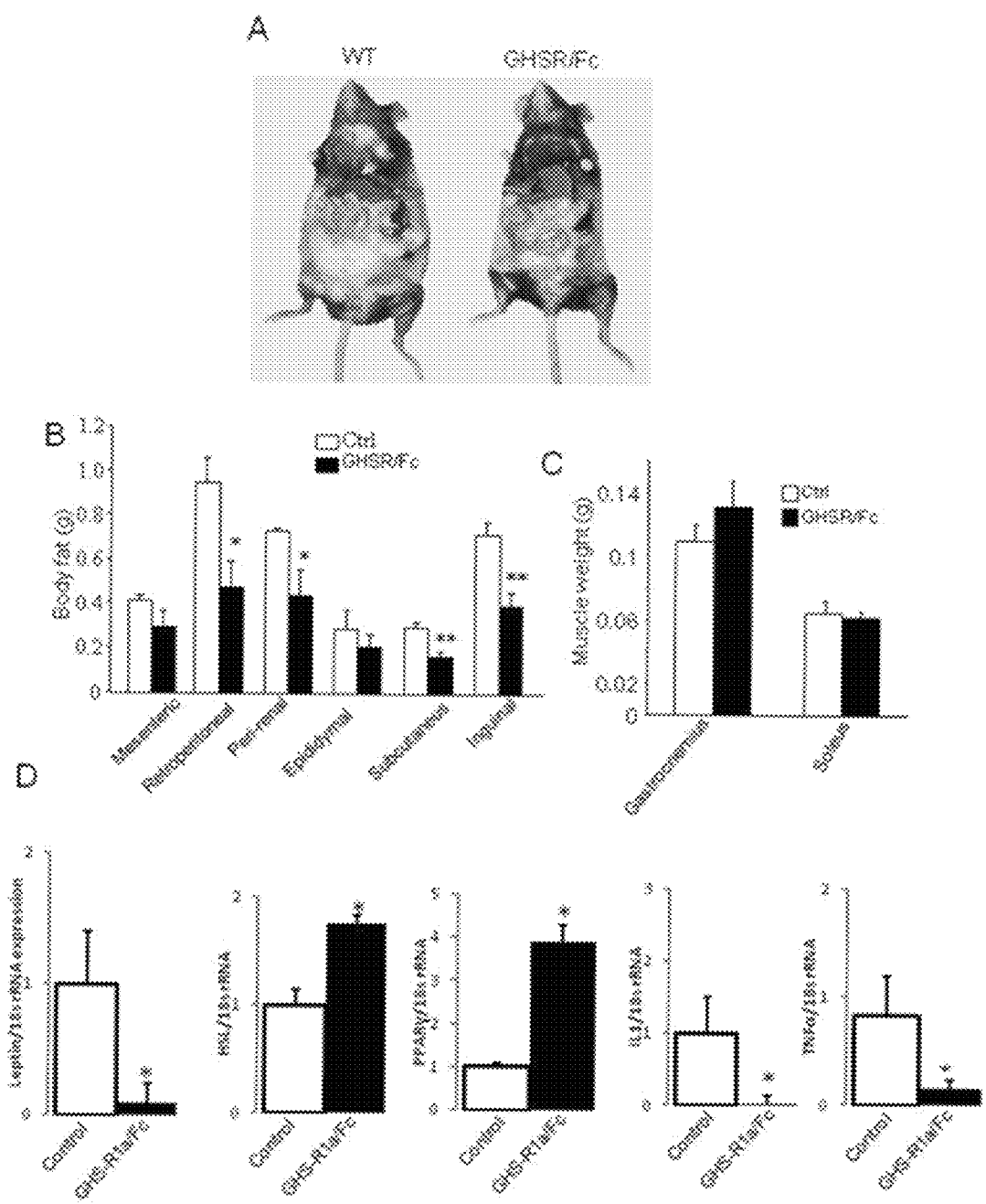
FIG. 4 shows the effect of GHSR/Fc on adipose tissue. Post experimentally, peritoneal fat pads were observed from sacrificed GHSR/Fc treated and control mice (A). Fat pad mass (B) and gastrocnemius muscle mass (C) were quantified for indicated stores in GHSR/Fc and control mice (B). mRNA Transcripts levels of leptin, hormone sensitive lipase (HSL), PPARγ, interleukin-1 (IL-1) and tumor necrosis factor α (TNFα) were quantified by real time RT-PCR relative to 18S ribosomal RNA using the standard curve method (D). Data are Mean±SEM, *$P<0.05$, **$p<0.001$, (n=5).

To determine the source of the reduced weight gain in the treated animals, fat pad and lean tissue (gastrocnemius and soleus muscles) were investigated. Visually, the amount of white adipose tissue (WAT) found in the peritoneum of treated mice was less than control (FIG. 4A). This difference was quantified by the weighing of various fat pads. Several fat stores were significantly smaller in the treated mice including retroperitoneal (0.476±0.12 g vs 0.948±0.119 g in control, $p<0.001$), peri-renal (0.44±0.19 g vs 0.734±0.011 g in control, $p<0.05$) and inguinal fat pads (0.396±0.067 g vs 0.722±0.56 g in control, $p<0.05$) (FIG. 4B). Lean mass was not affected by treatment as determined by the equal gastrocnemius muscle weight (0.131±0.016 g vs 0.109±0.011 g in control) (FIG. 4C).

Since reduced caloric consumption was not responsible for the reduction in WAT, alterations in WAT mRNA expression in the context of several metabolic genes were examined. Visceral WAT was examined for the adipokine leptin (a hormone that signals in response to fat cell anabolism), hormone sensitive lipase (HSL; an enzyme catalyzing the breakdown of triglycerides to fatty acids) and PPARγ (a nuclear receptor that promotes adipogenesis) mRNA using quantitative RT-PCR. Treated animals had lower levels of leptin gene expression in WAT (0.10±0.14 fold of control, $p<0.05$) while HSL mRNA (1.76±0.07 fold of control, $p<0.05$) and PPARγ mRNA (3.91±0.378 fold of control, $p<0.05$) expression were elevated (FIG. 4D). In addition, mRNA levels of adipose-derived proinflammatory cytokines known to be elevated in obesity were examined in WAT. Both interleukin-1 (IL-1) and tumor necrosis factor α (TNFα) were reduced in GHSR/Fc compared to control (2.9±1.6% of control for IL-1, and 15±7% of control for TNFα, $p<0.05$).

Effect of Neutralizing Ghrelin on Glucose Metabolism

Figure 5:
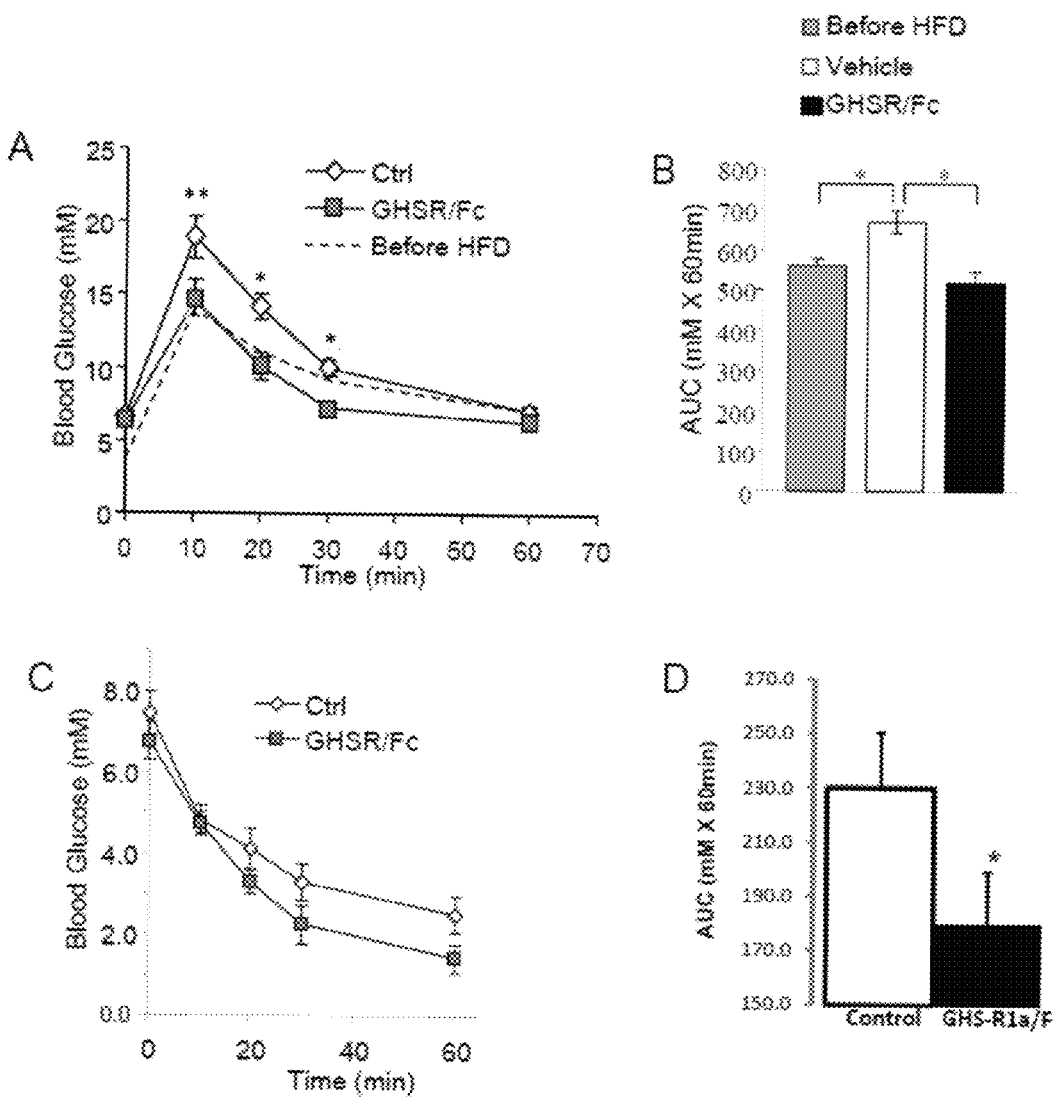
FIG. 5 shows intra-peritoneal glucose and insulin tolerance tests. Glucose tolerance test (IPGTT) were performed either prior to HFD feeding and before the metabolic cage assay (A). The area under the curve (AUC) for the glucose tolerance test was compared between GHSR/Fc and control mice (B). Insulin tolerance test (ITT) was conducted at the day before sacrifice of the mice (C), and (AUC) is shown (D). Data are Mean±SE, *$P<0.05$, ** $p<0.01$, (n=5).

Ghrelin has been shown to affect glucose homeostasis (Broglio, Arvat et al. 2001). To determine the effect of GHSR/Fc treatment on glucose metabolism, intra-peritoneal glucose tolerance tests (IPGTT) and insulin tolerance tests (ITT) were performed on control and treated mice before and at the end of the study. Treated mice displayed improved glucose tolerance with significantly lower blood glucose at 10 minutes (14.5±1.52 mmol/L vs 18.9±1.48 mmol/L in control, $p<0.01$) and 20 minutes (10.1±0.968 mmol/L vs 14.2±0.989 mmol/L in control, $p<0.05$) post glucose injection (FIG. 5A). The area under the curve in the IPGTT was also significantly decreased in the treated mice (516±32.2 vs 668±22.1 in control, $p<0.05$) (FIG. 5B). In ITT, area under the glucose curve was lower in treated animals (180±19.1 vs 230±20.3 in control, $p<0.05$) indicating increased insulin sensitivity (FIGS. 5C and 5D). These results suggest that reduced circulating AG improves insulin sensitivity and glucose tolerance in mice on a high fat diet.

Discussion

In this study, an in vivo gene transfer method was used to administer GHSR1a-based fusion proteins as a 'decoy receptor' for circulating AG in mice. The fusion constructs were designed to incorporate the extracellular domains of the GHSR1a that interact with the acylated portion of ghrelin, fused with IgG Fc to improve the stability and half-life of the complex in circulation (Soltani, Kumar et al. 2007). Initially, expression and secretion of the construct in vitro was confirmed by plasmid transfection in L6 muscle and CHO cell lines. As expected, the full length WT/Fc was not detected in culture media as it possesses the hydrophobic transmembrane domains that would retain it in the plasma membrane. The expression was further confirmed in both the muscle and plasma from GHSR/Fc plasmid injected animals. To verify that the treatment led to altered ghrelin levels both total (AG+UAG) and acylated (AG) levels were measured in the circulation. While there was no significant difference in the levels of total ghrelin, there was a significant reduction of AG in treated animals. Any differences in AG (5% of total ghrelin in circulation) occurring in the total ghrelin assay would likely be undetectable (Kojima, Hosoda et al. 1999; Ariyasu, Takaya et al. 2001). The lack of difference in the total ghrelin assay confirms the specificity of the GHSR/Fc for binding only AG.

The impact of neutralizing ghrelin on energy homeostasis was examined by placing animals on a HFD. Thirty days after the HFD feeding, animals treated with GHSR/Fc had gained significantly less weight compared to empty vector treated mice on high fat diet. The reduced weight gain in the GHSR/Fc group was maintained until the end of the study at 74 days post gene transfer with a final weight gain reduction of over 20%. These observations of reduced weight gain and reduced circulating AG in GHSR/Fc mice is in agreement with previous work examining the effects of ghrelin immunoneutralization (Zorrilla, Iwasaki et al. 2006).

Constructs encoding for the N-terminal region of the GHSR1a (Nt/Fc) or the N-terminal and the first extracellular loop (Nt-EC1/Fc) were also designed. These constructs, while exerting some weight sparing effects, had only a moderate effect compared with GHSR/Fc. The GHSR/Fc was the one construct that incorporated all 3 of the extracellular domains of the GHSR1a (Nt, EC1 and EC2). Without wishing to be bound by theory, of potential importance was the incorporation of both the extracellular loop domains (EC1 and EC2) as these extracellular loops are thought to be the binding sites for AG to the GHS-R1a (Pedretti, Villa et al. 2006).

Despite the difference in weight gain, no difference was observed throughout the study in food consumed between the GHSR/Fc treatment and control groups. Interestingly, the GHSR/Fc mice showed increased water consumption and urine output. Ghrelin's action on appetite occurs through binding with the GHSR1a in neurons within the arcuate nucleus of the hypothalamus (Cowley, Smith et al. 2003). While peripheral ghrelin administration has been shown to cross the blood brain barrier (BBB) and stimulate appetite (Banks, Tschop et al. 2002), a population of ghrelin-producing neurons also exists within the arcuate nucleus (Kageyama, Kitamura et al. 2008). In the present study, due to the size of the GHSR/Fc protein, it is unlikely that it was able to cross the BBB and neutralize hypothalamic ghrelin. Thus, without wishing to be bound by theory, the present strategy may only be targeting peripheral ghrelin and its actions. In agreement with this study, ghrelin immunoneutralization studies also had no effect on food intake (Zorrilla, Iwasaki et al. 2006). Furthermore, studies that examined both ghrelin and GHSR1a embryonic knockout mice also had no effect on feeding behavior but instead, when challenged with a high fat diet, were more likely to utilize fat as their energy substrate (Wortley, Anderson et al. 2004; Zigman, Nakano et al. 2005). Consistent with these previous observations, reduced fat pads primarily in the peritoneum were found in the present study.

Given that the food consumption was unchanged in GHSR/Fc-treated mice, the reduced fat mass is likely the consequence of the reduction in AG which affected fat tissue metabolism. Indeed, a recent study indicated that ghrelin acts directly on adipocytes to prevent lipolysis (Davies, Kotokorpi et al. 2009). To determine the effect of reduced circulating ghrelin levels on adipose tissue, the mRNA expression of fat metabolism genes in WAT was measured. Not surprisingly, leptin, which is produced during fat accumulation and adipocyte differentiation (Houseknecht, Baile et al. 1998), was lower in the GHSR/Fc-treated animals. Of particular interest, HSL, a key enzyme in the catabolism of triglycerides to fatty acids (Yeaman 2004), was found to be elevated in the treated animals. This increased lipase expression is indicative of increased mobilization of fatty acids for energy substrate, which supports the finding that the treated animals were protected from adiposity while eating a HFD. This finding is also in good agreement with a previous indirect calorimetry study on ghrelin KO mice that suggested preferential use of fat as their energy substrate (Wortley, Anderson et al. 2004).

PPARγ mRNA levels were also found to be elevated in the treated animals. While activation of this nuclear receptor typically leads to the differentiation and growth of adipose tissue, some evidence suggests that increased PPARγ may partition fat away from visceral stores (Laplante, Sell et al. 2003). Indeed, the present study shows that the most significant reduction on fat pad weight, in GHSR/Fc-treated mice was in the visceral depots. These findings are supported by other's studies that showed that low dose ghrelin administration caused increased fat pad weight and altered adipocyte gene expression without an effect on feeding in mice (Tsubone, Masaki et al. 2005). Taken together, the present data suggest that reducing circulating AG with GHSR-1a/Fc treatment leads to reduced fat stores and altered adipocyte gene expression.

Reducing AG with GHSR/Fc treatment significantly improved glucose tolerance and insulin sensitivity in mice on HFD feeding. These findings are in agreement with several studies suggesting that ghrelin promotes glucose homeostasis through inhibiting insulin release from the pancreas (Dezaki, Sone et al. 2006; Dezaki, Sone et al. 2008). Since no differences in circulating insulin levels were observed, the improved glucose clearance may be a consequence of reduced hepatic glucose production in the GHSR/Fc treated animals. This is, at least in part, supported by previous investigation that demonstrated that ghrelin promotes glucose production in hepatocytes(Gauna, Delhanty et al. 2005). Moreover, the improved glucose tolerance may be a secondary effect to the reduced visceral adiposity in GHSR/Fc-mice. It is known that increased adiposity can lead to insulin resistance which is brought on by proinflammatory factors released from inflamed fat stores (Oliver, McGillicuddy et al. 2010).

To determine the possible involvement of pro-inflammatory cytokines, the mRNA expression of both IL-1 and TNFα was examined in visceral adipose tissue. Both these genes were expressed at significantly lower levels in GHSR/Fc-treated animals, suggesting that improved insulin sensitivity in GHSR/Fc-treated mice may be partially conferred by reduced pro-inflammatory cytokines in these mice. Therefore, the strategy involving neutralization of circulating ghrelin, exemplified by the GHSR/Fc treatment, prevents weight gain and improves glucose tolerance, which may provide beneficial therapies for T2DM.

The present inventors examined if the GHSR/Fc treatment had any impact on other metabolic hormones. None of the hormones examined (GLP-1, insulin, PYY, pancreatic polypeptide and glucose insulinotropic peptide) were significantly altered by the expression of GHSR/Fc (data not shown). As ghrelin is a known GH secretagogue (Kojima, Hosoda et al. 1999) and GH has effects on glucose metabolism and insulin sensitivity (Moller and Jorgensen 2009), the effects of ghrelin depletion on GH were examined. Since GH varies throughout the day in a pulsatile fashion a more stable measurement of GH levels can be obtained by measuring circulating IGF-1. Interestingly, circulating IGF-1 levels were not affected by ghrelin neutralization and likely were not responsible for the reduced weight and improved glucose parameters. This lack of effect is consistent with a previous report indicating that GH levels are unchanged in GHSR1a KO mice on HFD (Zigman, Nakano et al. 2005).

In summary, a novel strategy has been developed using secretable GHSR1a-based fusion proteins to neutralize the circulating active ghrelin and hence reduce HFD-induced weight gain. Among those fusion constructs, the GHSR/Fc which contains the Nt, EC1, and EC2 domains of GHSR1a was the most effective in reducing weight gain, improving insulin resistance, and improving glucose tolerance in mice fed with HFD. Of particular benefit, this approach reduced body weight and adiposity, without affecting the appetite and, more particularly, lean mass. The treatment also altered adipose gene expression, exemplified by increased fat catabolism and reduced pro-inflammatory cytokines genes, suggesting a shift to fat usage rather than storage in mice. This yields a secondary beneficial outcome exemplified by improved insulin sensitivity and improved glucose clearance. Thus, GHSR/Fc fusion proteins may have clinical application for the treatment and management of obesity and T2DM.

Methods

Construct Design

All ghrelin receptor constructs were designed based on the mouse growth hormone secretagogue receptor sequence (Gene ID: 208188). GHSR regions and mouse IgG Fc fragment were produced by PCR amplification. Primers used for amplification of the N-terminal region were (6mNtF) GCG GGG TAC CAT GTG GAA CGC GAC GCC A (SEQ ID NO:19) and (6mNtR) GCG AGT ACT CGC GGG GAA CAG TGG CAG CAG TTC (SEQ ID NO:20), the first extracellular loop (6mEC1F) GCG AAG CTT TTC CAG TTT GTC AGC GAG AGC TGC ACC TAC GCC CCC AGC GAG ACC GTC ACC TGC (SEQ ID NO:21) and (6mEC1R) CGA AGC TTG CAG AGC AGG TCG CCG AAG TTC CAG GGC CGA TAC TGC CAG AGG CGC GCG GGG AAC AGT GGC AGC AGT TC (SEQ ID NO:22), the second extracellular loop (6mEC2F) GCG ACG GAT CCC CGG GAC ACC AAC GAG TGC CGC GCC ACC GAG TTC GCT GTG CGC TCT CCC AGC GAG ACC GTC ACC TGC AAC (SEQ ID NO:23) and (6mEC2R) GCGGGGATCCGTG CCG TTC TCG TGC TCC ACG CCC ACC AGC ACG GCG TAG GTG CAG CTC TCG CTG AC (SEQ ID NO:24), and mouse IgG Fc fragment (mIgGF) GCG AGT ACT TGG CCC AGC GAG ACC GTC ACC TGC AAC (SEQ ID NO:25) and (mIgGR) GCG CTC GAG CAG GGA AGA AGT CTG TTA TCA TGC A (SEQ ID NO:26). Each extracellular domain GHSR PCR product was cleaved with KpnI and ScaI while the mouse IgG Fc fragment was cleaved with ScaI and XhoI. This was ligated into the pSecTag2B vector (Invitrogen, ON Canada) at Kpn1 and XhoI using T4 DNA ligase.

Similar cloning strategy can be utilized for creating fusion molecules comprising the N-terminal, extracellular loop 1 and/or extracellular loop 2 of the mouse or human GHS-R1a.

In Vitro Expression of the Fusion Constructs

To establish the expression and secretion of GHSR constructs, the rat skeletal muscle cell line L6 and the Chinese hamster ovary CHO cells were transfected with the designed plasmids. 40 μg of cell extract and media were collected using standard methods and run out on 12% SDS PAGE gels. Following the end of experiments, the gastrocnemius muscle was collected and extracted from treated mice to examine the in vivo expression. Proteins were transferred to PVDF membrane and probed using anti-Myc antibody (Millipore) at 1:3000 at 4° C. followed by secondary rabbit ant-mouse HRP at 1:5000 at room temp for 1 hr.

Immunofluorescence Microscopy

To determine the localization and expression of transfected GHSR proteins, cell lines were immunostained with anti-IgG Fc antibodies which only detect the F chain of the transfected protein. L6 cells were grown on coverslips and were fixed for 1 hr at RT in 4% paraformaldehyde. They were then washed 3 times in PBS followed by 15 minutes of blocking in 5% normal horse serum. Cells were incubated with primary biotinylated anti-mouse Fc in blocking solution for 2 hours at room temperature (RT). Cells were then washed and treated with avidin-conjugated Cy3 in blocking solution for 45 minutes in dark at RT. Coverslips were mounted on slides and visualized on a Zeiss Axioplan II microscope.

In Vivo Expression of GHSR/Fc in Mice

C57/Bl6 mice were purchased from Jackson Laboratories (Bar Harbor, Me., USA). Mice were housed under controlled light (12 h light/12 h dark) and temperature conditions, and had free access to food (normal rodent chow, or high fat-diet where indicated) and water. All procedures were conducted in accordance with the guidelines of the Canadian Council on Animal Care and were approved by the St. Michael's Hospital Animal Care Committee.

In vivo expression of GHSR/Fc was achieved by intramuscular plasmid injection followed by an electroporation as previously described (Soltani, Kumar et al. 2007). Briefly, a total of 50 μg of plasmid DNA was injected (25 μg per leg) intramuscularly into gastrocnemius of 8 week old male C57/Bl6 mice and an electrical current was applied using caliper electrodes (BTX, MA) on the muscle as follows; 8 pulses (pulse length 20 ms) with 1 second intervals at 200V/cm. A conductive (aquasonic 100) gel was used to facilitate current delivery. Plasmid injection and electroporation were conducted once weekly for the first 3 weeks of the study course.

Food Intake and Body Weight Measurement:

High fat diet (Research diets, North Brunswick, N.J., USA, containing 60% of kCal as fat) began on the day of the first DNA injection and continued until the end of the experiment 54 days later. Food consumption was measured by weighing of food basket in each cage every 3 days. Animals from each group were weighed individually every 3 days.

Glucose and Insulin Tolerance Tests:

Intraperitoneal (ip) glucose and insulin tolerance tests were completed after 54 days of high fat diet. Animals were fasted overnight for 12 hours prior to tests. For the IPGTT, a single bolus injection of glucose at 1.5 mg/kg of mouse weight was administered ip. For the ITT, a single bolus injection of insulin at 0.75 U/kg was injected ip. Tails tips were treated with topical anesthetic (EMLA, ON Canada) and blood samples were drawn from tail vein at 0, 10, 20, 30, and 60 minutes post injection. Blood samples (4-5 μl) were analyzed by the glucose oxidase method using the Bayer Acensia Elite XL glucometer (Bayer, ON Canada).

Fat Tissue Collection

Post mortem analysis of fat tissues weight was completed by bi-lateral harvesting of fat pads and immediate weighing. The peritoneal fat tissue was snap frozen in liquid nitrogen for later RNA extraction.

Real Time PCR

Visceral white adipose tissue was collected at the end of the experiment. Total RNA was extracted using the Trizol® (Invitrogen, CA USA) extraction phenol chloroform precipitation method as per manufacturer's protocol. Samples were treated with DNAase (Invitrogen) and cDNA was produced using random hexamers under standard methods. Realtime PCR was conducted on the Bio-Rad CFX instrument (Bio-Rad, CA USA) using primers for leptin (forward: CCAAAACCCTCATCAAGACC (SEQ ID NO:27), reverse: TGTCTCCACCACCGAAACTC (SEQ ID NO:28)), hormone sensitive lipase (forward: TGTCTC-CACCACCGAAACTC (SEQ ID NO:29), reverse TCTC-CAGTTGAACCAAGCAGGTCA (SEQ ID NO:30)), PPARγ (forward: GGAAAGACAACGGACAAATCAC (SEQ ID NO:31), reverse: ATCCTTGGCCCTCTGAGATG (SEQ ID NO:32)), IL-1 (forward: TGTCTGAAGCAGC-TATGGCAA (SEQ ID NO:33, reverse: TGCTGCGA-GATTTGAAGCTG (SEQ ID NO:34)) and TNFα (forward: TGATCGGTCCCCAAAGGGAT (SEQ ID NO:35), reverse: TTGCTACGACGTGGGCTAC (SEQ ID NO:36)). Data was analyzed using Bio-Rad CFX manager software and relative expression was determined using the standard curve method with 18S as the normalization gene.

Hormone Assays

Blood was collected at the end of the experiment in capillary tubes containing EDTA (Sarstedt, PQ) from ad-libitum fed mice. Plasma level of hormones involved in the regulation of energy metabolism was analyzed using the Milliplex hormone assay panel (Millipore, MA) including; active GLP-1, insulin, PYY, pancreatic polypeptide, and GIP (Millipore). Acylated ghrelin and IGF-1 plasma levels were analyzed by enzyme link immunoassays (Cayman chemical, ON and Millipore, MA respectively) and total ghrelin levels were measured using a radioimmunoassay (Phoenix Pharmaceuticals, CA).

Statistical Analysis

The relative changes in weight gain over time were analyzed using the two-way ANOVA with Bonferroni post test to compare each group to the control group. Multiplex hormone assays analyzing each group were compared with the one-way ANOVA. Time points during IPGTT and ITT were examined by two-way ANOVA. All other comparisons between the control and GHSR/Fc group were analyzed with the student's t-test.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Sequences mNo6Nt-EC1-EC2-mIgG(nucleic acid) (SEQ ID NO: 1)

```
  1  atggatgcca tgaagagagg gctctgctgt gtgctgctgc tgtgtggagc agtcttcgtt
 61  tcgaacagcg agagcgacac gcgtcggaaa cggatgtgga acgcgacgcc cagcgaggag
121  ccggagccta acgtcacgct ggacctggac tgggacgctt ctcccggcaa cgactcactc
181  tctgacgaac tgctgccact gttccccgcg cgcctctggc agtatcggcc ctggaacttc
241  ggcgacctgc tctgcaaact cttccagttt gtcagcgaga gctgcaccgt gggcgtggag
301  cacgagaacg gcacagatcc ccgggacacc aacgagtgcc gcgccaccga gttcgctgtg
361  cgctctggcg gcggcggacc cagcgagacc gtcacctgca acgttgccca cccggccagc
421  agcaccaagg tggacaagaa aattgtgccc agggattgtg gttgtaagcc ttgcatatgt
481  acagtcccag aagtatcatc tgtcttcatc ttccccccaa agcccaagga tgtgctcacc
541  attactctga ctcctaaggt cacgtgtgtt gtggtagaca tcagcaagga tgatcccgag
601  gtccagttca gctggtttgt agatgatgtg gaggtgcaca cagctcagac gcaacccgg
661  gaggagcagt tcaacagcac tttccgctca gtcagtgaac ttcccatcat gcaccaggac
721  tggctcaatg gcaaggagtt caaatgcagg gtcaacagtg cagctttccc tgcccccatc
781  gagaaaacca tctccaaaac caaaggcaga ccgaaggctc cacaggtgta caccattcca
841  cctcccaagg agcagatggc caaggataaa gtcagtctga cctgcatgat aacagacttc
901  ttccctgctc gaggagggcc cgaacaaaaa ctcatctcag aagaggatct gaatagcgcc
961  gtcgaccatc atcatcatcat
``` mNo6 Nt-EC1-EC2-mIgG amino acid sequence (SEQ ID NO: 2)

MDAMKRGLCCVLLLCGAVFVSNSESDTRRKRMWNATPSEEPEPNVTLDLDWDASPGNDSL

SDELLPLFPARLWQYRPWNFGDLLCKLFQFVSESCTVGVEHENGTDPRDTNECRATEFAV

RSGGGGSRKCCVECPPCPAPPVAGPSVFLFPPKPKDPLMISRTPEVTCVVVDVSHEDPEV

QFNWYVDGVEVHNAKTKPREEQFNSTFRVVSVLTVVHQDWLNGKEYKCKVSNKGLPAPIE

KTISKTKGQPREPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLSLSPGK--RPRI

PRPRPLAN

Mouse N-Terminal Domain (nucleic acid) (SEQ ID NO: 3)

```
  1  atgtggaacg cgacgcccag cgaggagccg gagcctaacg tcacgctgga cctggactgg
 61  gacgcttctc ccggcaacga ctcactctct gacgaactgc tgccactgtt ccccgcg
```

Mouse N-Terminal Domain (amino acid) (SEQ ID NO: 4)

MWNATPSEEPEPNVTLDLDWDASPGNDSLSDELLPLFPA

TABLE 1-continued

Sequences

Mouse EC1 Domain (nucleic acid) (SEQ ID NO: 5)

```
  1  cgcctctggc agtatcggcc ctggaacttc ggcgacctgc tctgcaaact cttccagttt
 61  gtcagcgaga gctgcacc
```

Mouse EC1 Domain (amino acid) (SEQ ID NO: 6)

RLWQYRPWNFGDLLCKLFQFVSESCT

Mouse EC2 Domain (nucleic acid) (SEQ ID NO: 7)

```
  1  gtgggcgtgg agcacgagaa cggcacagat ccccgggaca ccaacgagtg ccgcgccacc
 61  gagttcgctg tgcgctct
```

Mouse EC2 Domain (amino acid) (SEQ ID NO: 8)

VGVEHENGTDPRDTNECRATEFAVRS

Mouse Ghrelin receptor (nucleic acid) (SEQ ID NO: 9)

```
   1  atgtggaacg cgacgcccag cgaggagccg gagcctaacg tcacgctgga cctggactgg
  61  gacgcttctc ccggcaacga ctcactctct gacgaactgc tgccactgtt ccccgcgccg
 121  ctgctggcgg gcgtcactgc cacctgcgtg gcgctcttcg tggtgggcat ctcgggcaac
 181  ctgctcacca tgctggtggt gtcccgcttc cgcgagctgc gcaccaccac caacctctac
 241  ctatccagca tggccttctc cgatctgctc atcttcctgt gcatgccgct ggacctcgtc
 301  cgcctctggc agtatcggcc ctggaacttc ggcgacctgc tctgcaaact cttccagttt
 361  gtcagcgaga gctgcaccta cgccacggtc ctcaccatca ccgcgctgag cgtcgagcgc
 421  tacttcgcca tctgcttccc gctgcgggcc aaggtggtgg tcaccaaggg ccgtgtgaag
 481  ctggtcatcc ttgtcatttg ggccgtggcc ttctgcagcg cggggcccat cttcgtgctg
 541  gtgggcgtgg agcacgagaa cggcacagat ccccgggaca ccaacgagtg ccgcgccacc
 601  gagttcgctg tgcgctctgg gctgctcacc gtgatggtat gggtgtcgag cgtcttcttc
 661  ttcctgccgg tcttctgcct cactgtgctc tacagtctca tcgggaggaa gctgtggcgg
 721  aggcgcggcg acgcggcggt gggctcctcg ctcagggacc agaaccacaa acagacagtg
 781  aagatgcttg ctgtggtggt gtttgctttc atcctctgct ggctgccctt ccacgtggga
 841  agatatctgt tttccaagtc tttcgagcct ggctctctgg agatcgcgca gatcagtcag
 901  tactgcaacc tggtgtcctt tgtcctcttc tacctcagcg ctgccatcaa ccccattctc
 961  tacaacatca tgtccaagaa gtaccgggtg ccgtgttca aacttctagg atttgaatcc
1021  ttctcccaga gaaagctttc cactctgaag gatgagagtt cccgggcctg gacaaagtcg
1081  agcatcaata catga
```

Human Fusion molecule (nucleic acid) (SEQ ID NO: 10)

```
   1  atggatgcca tgaagagagg gctctgctgt gtgctgctgc tgtgtggagc agtcttcgtt
  61  tcgaacagcg agagcgacac gcgtcggaaa cggatgtgga acgcgacgcc cagcgaagag
 121  ccggggttca acctcacact ggccgacctg actgggatg cttcccccgg caacgactcg
 181  ctgggcgacg agctgctgca gctcttcccc gcgcgcctct ggcagtaccg gccctggaac
 241  ttcggcgacc tcctctgcaa actcttccaa ttcgtcagtg agagctgcac cgtcggggtg
 301  gagcacgaga acggcaccga cccttgggac accaacgagt gccgcccac cgagtttgcg
 361  gtgcgctctg cggcggcgg atctagaaaa tgttgtgtcg agtgccacc gtgcccagca
 421  ccacctgtgg caggaccgtc agtcttcctc ttccccccaa aacccaagga cccctcatg
```

TABLE 1-continued

Sequences

```
 481   atctcccgga cccctgaggt cacgtgcgtg gtggtggacg tgagccacga agaccccgag
 541   gtccagttca actggtacgt ggacggcgtg gaggtgcata atgccaagac aaagccacgg
 601   gaggagcagt tcaacagcac gttccgtgtg gtcagcgtcc tcaccgttgt gcaccaggac
 661   tggctgaacg gcaaggagta caagtgcaag gtctccaaca aaggcctccc agcccccatc
 721   gagaaaacca tctccaaaac caagggcag ccccgagaac acaggtgta caccctgccc
 781   ccatcccggg aggagatgac caagaaccag gtcagcctga cctgcctggt caaaggcttc
 841   taccccagcg acatcgccgt ggagtgggag agcaatgggc agccggagaa caactacaag
 901   accacacctc ccatgctgga ctccgacggc tccttcttcc tctacagcaa gctcaccgtg
 961   gacaagagca ggtggcagca ggggaacgtc ttctcatgct ccgtgatgca tgaggctctg
1021   cacaaccact acacgcagaa gagcctctcc ctgtctccgg gtaaatgata gcggccgcgg
1081   atcccccgac ctcgacctct ggctaat
```

Human Fusion molecule (amino acid) (SEQ ID NO: 11)

MDAMKRGLCCVLLLCGAVFVSNSESDTRRKRMWNATPSEEPGFNLTLADLDWDASPGNDS
LGDELLQLFPARLWQYRPWNFGDLLCKLFQFVSESCTVGVEHENGTDPWDTNECRPTEFA
VRSGGGGSRKCCVECPPCPAPPVAGPSVFLEPPKPKDPLMISRTPEVTCVVVDVSHEDPE
VQFNWYVDGVEVHNAKTKPREEQFNSTFRVVSVLTVVHQDWLNGKEYKCKVSNKGLPAPI
EKTISKTKGQPREPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSLSLSPGK

Human N-Terminal Domain (nucleic acid) (SEQ ID NO: 12)

```
  1   atgtggaacg cgacgcccag cgaagagccg gggttcaacc tcacactggc cgacctggac
 61   tgggatgctt cccccggcaa cgactcgctg ggcgacgagc tgctgcagct cttccccgcg
```

Human N-Terminal Domain (amino acid) (SEQ ID NO: 13)

MWNATPSEEPGFNLTLADLDWDASPGNDSLGDELLQLFPA

Human EC1 Domain (nucleic acid) (SEQ ID NO: 14)

```
  1   cgcctctggc agtaccggcc ctggaacttc ggcgacctcc tctgcaaact cttccaattc
 61   gtcagtgaga gctgcacc
```

Human EC1 Domain (amino acid) (SEQ ID NO: 15)

RLWQYRPWNFGDLLCKLFQFVSESCT

Human EC2 Domain (nucleic acid) (SEQ ID NO: 16)

```
  1   gtcggggtgg agcacgagaa cggcaccgac ccttgggaca ccaacgagtg ccgccccacc
 61   gagtttgcgg tgcgctct
```

Human EC2 Domain (amino acid) (SEQ ID NO: 17)

VGVEHENGTDPWDTNECRPTEFAVRS

Human Ghrelin receptor (nucleic acid) (SEQ ID NO: 18)

```
  1   atgtggaacg cgacgcccag cgaagagccg gggttcaacc tcacactggc cgacctggac
 61   tgggatgctt cccccggcaa cgactcgctg ggcgacgagc tgctgcagct cttccccgcg
121   ccgctgctgg cgggcgtcac agccacctgc gtggcactct tcgtggtggg catcgctggc
181   aacctgctca ccatgctggt ggtgtcgcgc ttccgcgagc tgcgcaccac caccaacctc
241   tacctgtcca gcatggcctt ctccgatctg ctcatcttcc tctgcatgcc cctggaccctc
```

TABLE 1-continued

Sequences

```
 301    gttcgcctct ggcagtaccg gccctggaac ttcggcgacc tcctctgcaa actcttccaa
 361    ttcgtcagtg agagctgcac ctacgccacg gtgctcacca tcacagcgct gagcgtcgag
 421    cgctacttcg ccatctgctt cccactccgg gccaaggtgg tggtcaccaa ggggcgggtg
 481    aagctggtca tcttcgtcat ctgggccgtg gccttctgca gcgccgggcc catcttcgtg
 541    ctagtcgggg tggagcacga gaacggcacc gacccttggg acaccaacga gtgccgcccc
 601    accgagtttg cggtgcgctc tggactgctc acggtcatgg tgtgggtgtc cagcatcttc
 661    ttcttccttc ctgtcttctg tctcacggtc ctctacagtc tcatcggcag gaagctgtgg
 721    cggaggaggc gcggcgatgc tgtcgtgggt gcctcgctca gggaccagaa ccacaagcaa
 781    accgtgaaaa tgctggctgt agtggtgttt gccttcatcc tctgctggct cccttccac
 841    gtagggcgat atttattttc caaatccttt gagcctggct ccttggagat tgctcagatc
 901    agccagtact gcaacctcgt gtcctttgtc ctcttctacc tcagtgctgc catcaacccc
 961    attctgtaca acatcatgtc caagaagtac cgggtggcag tgttcagact tctgggattc
1021    gaaccctctc cccagagaaa gctctccact ctgaaagatg aaagttctcg ggcctggaca
1081    gaatctagta ttaatacatg a
```

REFERENCES

Ariyasu, H., K. Takaya, et al. (2001). "Stomach is a major source of circulating ghrelin, and feeding state determines plasma ghrelin-like immunoreactivity levels in humans." *J Clin Endocrinol Metab* 86(10): 4753-4758.

Banks, W. A., M. Tschop, et al. (2002). "Extent and direction of ghrelin transport across the blood-brain barrier is determined by its unique primary structure." *J Pharmacol Exp Ther* 302(2): 822-827.

Blackburn, G. (1995). "Effect of degree of weight loss on health benefits." *Obes Res* 3 Suppl 2:211s-216s.

Bosello, O., F. Armellini, et al. (1997). "The benefits of modest weight loss in type II diabetes." *Int J Obes Relat Metab Disord* 21 Suppl 1: S10-13.

Broglio, F., E. Arvat, et al. (2001). "Ghrelin, a natural GH secretagogue produced by the stomach, induces hyperglycemia and reduces insulin secretion in humans." *J Clin Endocrinol Metab* 86(10): 5083-5086.

Cowley, M. A., R. G. Smith, et al. (2003). "The distribution and mechanism of action of ghrelin in the CNS demonstrates a novel hypothalamic circuit regulating energy homeostasis." *Neuron* 37(4): 649-661.

Davies, J. S., P. Kotokorpi, et al. (2009). "Ghrelin induces abdominal obesity via GHS-R-dependent lipid retention." *Mol Endocrinol* 23(6): 914-924.

De Silva, A., V. Salem, et al. (2011). "The gut hormones PYY 3-36 and GLP-1 7-36 amide reduce food intake and modulate brain activity in appetite centers in humans." *Cell Metab* 14(5): 700-706.

Dezaki, K., H. Sone, et al. (2006). "Blockade of pancreatic islet-derived ghrelin enhances insulin secretion to prevent high-fat diet-induced glucose intolerance." *Diabetes* 55(12): 3486-3493.

Dezaki, K., H. Sone, et al. (2008). "Ghrelin is a physiological regulator of insulin release in pancreatic islets and glucose homeostasis." *Pharmacol Ther* 118(2): 239-249.

Gauna, C., P. J. Delhanty, et al. (2005). "Ghrelin stimulates, whereas des-octanoyl ghrelin inhibits, glucose output by primary hepatocytes." *J Clin Endocrinol Metab* 90(2): 1055-1060.

Gray, L. J., N. Cooper, et al. (2012). "A systematic review and mixed treatment comparison of pharmacological interventions for the treatment of obesity." *Obes Rev.*

Houseknecht, K. L., C. A. Baile, et al. (1998). "The biology of leptin: a review." *J Anim Sci* 76(5): 1405-1420.

Howard, A. D., S. D. Feighner, et al. (1996). "A receptor in pituitary and hypothalamus that functions in growth hormone release." *Science* 273(5277): 974-977.

Kageyama, H., Y. Kitamura, et al. (2008). "Visualization of ghrelin-producing neurons in the hypothalamic arcuate nucleus using ghrelin-EGFP transgenic mice." *Regul Pept* 145(1-3): 116-121.

Kamegai, J., H. Tamura, et al. (2000). "Central effect of ghrelin, an endogenous growth hormone secretagogue, on hypothalamic peptide gene expression." *Endocrinology* 141(12): 4797-4800.

Kojima, M., H. Hosoda, et al. (1999). "Ghrelin is a growth-hormone-releasing acylated peptide from stomach." *Nature* 402(6762): 656-660.

Laplante, M., H. Sell, et al. (2003). "PPAR-gamma activation mediates adipose depot-specific effects on gene expression and lipoprotein lipase activity: mechanisms for modulation of postprandial lipemia and differential adipose accretion." *Diabetes* 52(2): 291-299.

Moller, N. and J. O. Jorgensen (2009). "Effects of growth hormone on glucose, lipid, and protein metabolism in human subjects." *Endocr Rev* 30(2): 152-177.

Nakazato, M., N. Murakami, et al. (2001). "A role for ghrelin in the central regulation of feeding." *Nature* 409(6817): 194-198.

Neary, M. T. and R. L. Batterham (2009). "Gut hormones: implications for the treatment of obesity." *Pharmacol Ther* 124(1): 44-56.

Oliver, E., F. McGillicuddy, et al. (2010). "The role of inflammation and macrophage accumulation in the development of obesity-induced type 2 diabetes mellitus and the possible therapeutic effects of long-chain n-3 PUFA." *Proc Nutr Soc* 69(2): 232-243.

Pedretti, A., M. Villa, et al. (2006). "Construction of human ghrelin receptor (hGHS-R1a) model using a fragmental prediction approach and validation through docking analysis." *J Med Chem* 49(11): 3077-3085.

Pi-Sunyer, F. X. (1996). "A review of long-term studies evaluating the efficacy of weight loss in ameliorating disorders associated with obesity." *Clin Ther* 18(6): 1006-1035; discussion 1005.

Rodriguez, A., J. Gomez-Ambrosi, et al. (2009). "Acylated and desacyl ghrelin stimulate lipid accumulation in human visceral adipocytes." *Int J Obes (Lond)* 33(5): 541-552.

Soltani, N., M. Kumar, et al. (2007). "In vivo expression of GLP-1/IgG-Fc fusion protein enhances beta-cell mass and protects against streptozotocin-induced diabetes." *Gene Ther* 14(12): 981-988.

Tschop, M., D. L. Smiley, et al. (2000). "Ghrelin induces adiposity in rodents." *Nature* 407(6806): 908-913.

Tsubone, T., T. Masaki, et al. (2005). "Ghrelin regulates adiposity in white adipose tissue and UCP1 mRNA expression in brown adipose tissue in mice." *Regul Pept* 130(1-2): 97-103.

Wang, Y. C, K. McPherson, et al. (2011). "Health and economic burden of the projected obesity trends in the USA and the UK." *Lancet* 378(9793): 815-825.

Wortley, K. E., K. D. Anderson, et al. (2004). "Genetic deletion of ghrelin does not decrease food intake but influences metabolic fuel preference." *Proc Natl Acad Sci USA* 101(21): 8227-8232.

Yeaman, S. J. (2004). "Hormone-sensitive lipase—new roles for an old enzyme." *Biochem J* 379(Pt 1): 11-22.

Zhang, J. V., P. G. Ren, et al. (2005). "Obestatin, a peptide encoded by the ghrelin gene, opposes ghrelin's effects on food intake." *Science* 310(5750): 996-999.

Zhu, X., Y. Cao, et al. (2006). "On the processing of proghrelin to ghrelin." *J Biol Chem* 281(50): 38867-38870.

Zigman, J. M, Y. Nakano, et al. (2005). "Mice lacking ghrelin receptors resist the development of diet-induced obesity." *J Clin Invest* 115(12): 3564-3572.

Zorrilla, E. P., S. Iwasaki, et al. (2006). "Vaccination against weight gain." *Proc Natl Acad Sci USA* 103(35): 13226-13231.

The invention claimed is:

1. A soluble fusion molecule comprising
   a)
      i) the N-terminal of human growth hormone secretagogue receptor (GHS-R1a) having an amino acid sequence as shown in SEQ ID NO: 13 or a variant thereof with at least 95% sequence identity, linked to extracellular loop 1 (EC1) having an amino acid sequence as shown in SEQ ID NO: 15 or a variant thereof with at least 95% sequence identity
      ii) the N-terminal of GHS-R1a having an amino acid sequence as shown in SEQ ID NO: 13 or a variant thereof with at least 95% sequence identity, linked to extracellular loop 1 having an amino acid sequence as shown in SEQ ID NO: 15 or a variant thereof with at least 95% sequence identity, or
      iii) the N-terminal of GHS-R1a having an amino acid sequence as shown SEQ ID NO: 13 or a variant thereof with at least 95% sequence identity linked to extracellular loop 1 having an amino acid sequence as shown in SEQ ID NO: 15 or a variant thereof with at least 95% sequence identity and extracellular loop 2 having an amino acid sequence as shown SEQ ID NO: 17 or a variant thereof with at least 95% sequence identity; linked to; and
   b) a fusion partner that is an immunoglobulin G (IgG) constant region (Fc) of IgG 2 or IgG4.

2. The soluble fusion molecule of claim 1, wherein a) comprises or consists of i) the N-terminal, ii) the extracellular loop 1 and iii) the extracellular loop 2 of the human GHS-R1a.

3. The soluble fusion molecule of claim 1, wherein the N-terminal of human GHS-R1a is encoded by the nucleic acid sequence as shown in SEQ ID NO: 12 or a variant thereof with at least 95% sequence identity; wherein the extracellular loop 1 of human GHS R1a is encoded by the nucleic acid sequence as shown in SEQ ID NO: 14 or a variant thereof with at least 95% sequence identity; and/or wherein the extracellular loop 2 of human GHS R1a is encoded by a nucleic acid sequence as shown in SEQ ID NO: 16 or a variant thereof with at least 95% sequence identity.

4. The soluble fusion molecule of claim 1, wherein the Fc region is the Fc region of IgG2.

5. The soluble fusion molecule of claim 1, further comprising a peptide linker between a) and b).

6. The soluble fusion molecule of claim 1 comprising the amino acid sequence as shown in SEQ ID NO: 11 or a variant thereof with at least 95% sequence identity or encoded by the nucleic acid sequence as shown in SEQ ID NO: 10 or a variant thereof with at least 95% sequence identity.

7. A nucleic acid molecule encoding the soluble fusion molecule of claim 1.

8. A host cell comprising the nucleic acid molecule of claim 7.

9. A pharmaceutical composition comprising the soluble fusion molecule of claim 1, a nucleic acid molecule encoding said soluble fusion molecule or a host cell expressing said nucleic acid molecule, and a pharmaceutically acceptable carrier.

10. The pharmaceutical composition of claim 9 comprising the soluble fusion molecule and a pharmaceutically acceptable carrier.

* * * * *

SEQUENCE LISTING

```
<160> NUMBER OF SEQ ID NOS: 36

<210> SEQ ID NO 1
<211> LENGTH: 981
<212> TYPE: DNA
<213> ORGANISM: Artificial Sequence
<220> FEATURE:
<223> OTHER INFORMATION: Synthetic Construct

<400> SEQUENCE: 1
atggatgcca tgaagagagg gctctgctgt gtgctgctgc tgtgtggagc agtcttcgtt      60
tcgaacagcg agagcgacac gcgtcggaaa cggatgtgga acgcgacgcc cagcgaggag     120
ccggagccta acgtcacgct ggacctggac tgggacgctt ctcccggcaa cgactcactc     180
tctgacgaac tgctgccact gttccccgcg cgcctctggc agtatcggcc ctggaacttc     240
ggcgacctgc tctgcaaact cttccagttt gtcagcgaga gctgcaccgt gggcgtggag     300
cacgagaacg gcacagatcc ccgggacacc aacgagtgcc gcgccaccga gttcgctgtg     360
cgctctggcg gcggcggacc cagcgagacc gtcacctgca acgttgccca cccggccagc     420
agcaccaagg tggacaagaa aattgtgccc agggattgtg gttgtaagcc ttgcatatgt     480
acagtcccag aagtatcatc tgtcttcatc ttcccccccaa agcccaagga tgtgctcacc     540
attactctga ctcctaaggt cacgtgtgtt gtggtagaca tcagcaagga tgatcccgag     600
gtccagttca gctggtttgt agatgatgtg gaggtgcaca cagctcagac gcaacccgg      660 gaggagcagt tcaacagcac tttccgctca gtcagtgaac ttcccatcat gcaccaggac     720
tggctcaatg gcaaggagtt caaatgcagg gtcaacagtg cagctttccc tgcccccatc     780
gagaaaacca tctccaaaac caaaggcaga ccgaaggctc cacaggtgta caccattcca     840
cctcccaagg agcagatggc caaggataaa gtcagtctga cctgcatgat aacagacttc     900
ttccctgctc gaggagggcc cgaacaaaaa ctcatctcag aagaggatct gaatagcgcc     960
gtcgaccatc atcatcatca t                                              981

<210> SEQ ID NO 2
<211> LENGTH: 366
<212> TYPE: PRT
<213> ORGANISM: Artificial Sequence
```

<220> FEATURE:
<223> OTHER INFORMATION: Synthetic Construct

<400> SEQUENCE: 2

Met Asp Ala Met Lys Arg Gly Leu Cys Cys Val Leu Leu Leu Cys Gly
1               5                   10                  15

Ala Val Phe Val Ser Asn Ser Glu Ser Asp Thr Arg Arg Lys Arg Met
            20                  25                  30

Trp Asn Ala Thr Pro Ser Glu Glu Pro Glu Pro Asn Val Thr Leu Asp
        35                  40                  45

Leu Asp Trp Asp Ala Ser Pro Gly Asn Asp Ser Leu Ser Asp Glu Leu
    50                  55                  60

Leu Pro Leu Phe Pro Ala Arg Leu Trp Gln Tyr Arg Pro Trp Asn Phe
65                  70                  75                  80

Gly Asp Leu Leu Cys Lys Leu Phe Gln Phe Val Ser Glu Ser Cys Thr
                85                  90                  95

Val Gly Val Glu His Glu Asn Gly Thr Asp Pro Arg Asp Thr Asn Glu
            100                 105                 110

Cys Arg Ala Thr Glu Phe Ala Val Arg Ser Gly Gly Gly Ser Arg
        115                 120                 125

Lys Cys Cys Val Glu Cys Pro Cys Pro Ala Pro Val Ala Gly
    130                 135                 140

Pro Ser Val Phe Leu Phe Pro Pro Lys Pro Lys Asp Pro Leu Met Ile
145                 150                 155                 160

Ser Arg Thr Pro Glu Val Thr Cys Val Val Asp Val Ser His Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Phe Arg
        195                 200                 205

Val Val Ser Val Leu Thr Val Val His Gln Asp Trp Leu Asn Gly Lys
    210                 215                 220

Glu Tyr Lys Cys Lys Val Ser Asn Lys Gly Leu Pro Ala Pro Ile Glu
225                 230                 235                 240

Lys Thr Ile Ser Lys Thr Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Met
290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Arg Pro Arg Ile Pro Arg Pro Arg Pro Leu Ala Asn
        355                 360                 365

<210> SEQ ID NO 3
<211> LENGTH: 117
<212> TYPE: DNA
<213> ORGANISM: Mus musculus

```
<400> SEQUENCE: 3
atgtggaacg cgacgcccag cgaggagccg gagcctaacg tcacgctgga cctggactgg     60
gacgcttctc ccggcaacga ctcactctct gacgaactgc tgccactgtt ccccgcg       117

<210> SEQ ID NO 4
<211> LENGTH: 39
<212> TYPE: PRT
<213> ORGANISM: Mus Musculus

<400> SEQUENCE: 4

Met Trp Asn Ala Thr Pro Ser Glu Glu Pro Glu Pro Asn Val Thr Leu
1               5                   10                  15

Asp Leu Asp Trp Asp Ala Ser Pro Gly Asn Asp Ser Leu Ser Asp Glu
            20                  25                  30

Leu Leu Pro Leu Phe Pro Ala
        35

<210> SEQ ID NO 5
<211> LENGTH: 78
<212> TYPE: DNA
<213> ORGANISM: Mus Musculus

<400> SEQUENCE: 5
cgcctctggc agtatcggcc ctggaacttc ggcgacctgc tctgcaaact cttccagttt     60
gtcagcgaga gctgcacc                                                  78

<210> SEQ ID NO 6
<211> LENGTH: 26
<212> TYPE: PRT
<213> ORGANISM: Mus Musculus

<400> SEQUENCE: 6

Arg Leu Trp Gln Tyr Arg Pro Trp Asn Phe Gly Asp Leu Leu Cys Lys
1               5                   10                  15

Leu Phe Gln Phe Val Ser Glu Ser Cys Thr
            20                  25

<210> SEQ ID NO 7
<211> LENGTH: 78
<212> TYPE: DNA
<213> ORGANISM: Mus Musculus

<400> SEQUENCE: 7
gtgggcgtgg agcacgagaa cggcacagat ccccgggaca ccaacgagtg ccgcgccacc     60
gagttcgctg tgcgctct                                                  78

<210> SEQ ID NO 8
<211> LENGTH: 26
<212> TYPE: PRT
<213> ORGANISM: Mus Musculus

<400> SEQUENCE: 8

Val Gly Val Glu His Glu Asn Gly Thr Asp Pro Arg Asp Thr Asn Glu
1               5                   10                  15

Cys Arg Ala Thr Glu Phe Ala Val Arg Ser
            20                  25

<210> SEQ ID NO 9
<211> LENGTH: 1095
```

```
<212> TYPE: DNA
<213> ORGANISM: Mus Musculus

<400> SEQUENCE: 9
atgtggaacg cgacgcccag cgaggagccg gagcctaacg tcacgctgga cctggactgg      60
gacgcttctc ccggcaacga ctcactctct gacgaactgc tgccactgtt ccccgcgccg     120
ctgctggcgg gcgtcactgc cacctgcgtg gcgctcttcg tggtgggcat ctcgggcaac     180
ctgctcacca tgctggtggt gtcccgcttc cgcgagctgc gcaccaccac caacctctac     240
ctatccagca tggccttctc cgatctgctc atcttctgt gcatgccgct ggacctcgtc      300
cgcctctggc agtatcggcc ctggaacttc ggcgacctgc tctgcaaact cttccagttt     360
gtcagcgaga gctgcaccta cgccacggtc ctcaccatca ccgcgctgag cgtcgagcgc     420
tacttcgcca tctgcttccc gctgcgggcc aaggtggtgg tcaccaaggg ccgtgtgaag     480
ctggtcatcc ttgtcatttg ggccgtggcc ttctgcagcg cggggcccat cttcgtgctg     540
gtgggcgtgg agcacgagaa cggcacagat ccccgggaca ccaacgagtg ccgcgccacc     600
gagttcgctg tgcgctctgg gctgctcacc gtgatggtat gggtgtcgag cgtcttcttc     660
ttcctgccgg tcttctgcct cactgtgctc tacagtctca tcgggaggaa gctgtggcgg     720
aggcgcggcg acgcggcggt gggctcctcg ctcagggacc agaaccacaa acagacagtg     780
aagatgcttg ctgtggtggt gtttgctttc atcctctgct ggctgccctt ccacgtggga     840
agatatctgt tttccaagtc tttcgagcct ggctctctgg agatcgcgca gatcagtcag     900
tactgcaacc tggtgtcctt tgtcctcttc tacctcagcg ctgccatcaa ccccattctc     960
tacaacatca tgtccaagaa gtaccgggtg gccgtgttca aacttctagg atttgaatcc    1020
ttctcccaga gaaagctttc cactctgaag gatgagagtt cccgggcctg gacaaagtcg    1080
agcatcaata catga                                                     1095

<210> SEQ ID NO 10
<211> LENGTH: 1107
<212> TYPE: DNA
<213> ORGANISM: Artificial Sequence
<220> FEATURE:
<223> OTHER INFORMATION: Synthetic Construct

<400> SEQUENCE: 10
atggatgcca tgaagagagg gctctgctgt gtgctgctgc tgtgtggagc agtcttcgtt      60
tcgaacagcg agagcgacac gcgtcggaaa cggatgtgga acgcgacgcc cagcgaagag     120
ccggggttca acctcacact ggccgacctg actgggatg cttcccccgg caacgactcg      180
ctgggcgacg agctgctgca gctcttcccc gcgcgcctct ggcagtaccg gccctggaac     240
ttcggcgacc tcctctgcaa actcttccaa ttcgtcagtg agagctgcac cgtcggggtg     300
agcacgagaa acggcaccga cccttgggac accaacgagt gccgccccac cgagtttgcg     360
gtgcgctctg gcgcggcgg atctagaaaa tgttgtgtcg agtgcccacc gtgcccagca     420
ccacctgtgg caggaccgtc agtcttcctc ttccccccaa acccaaggga ccccctcatg     480
atctcccgga cccctgaggt cacgtgcgtg gtggtggacg tgagccacga agaccccgag     540
gtccagttca actggtacgt ggacggcgtg gaggtgcata atgccaagac aaagccacgg     600
gaggagcagt tcaacagcac gttccgtgtg gtcagcgtcc tcaccgttgt gcaccaggac     660
tggctgaacg gcaaggagta caagtgcaag gtctccaaca aaggcctccc agcccccatc     720
gagaaaacca tctccaaaac caaagggcag ccccgagaac cacaggtgta caccctgccc     780
```

```
ccatcccggg aggagatgac caagaaccag gtcagcctga cctgcctggt caaaggcttc      840
taccccagcg acatcgccgt ggagtgggag agcaatgggc agccggagaa caactacaag      900
accacacctc ccatgctgga ctccgacggc tccttcttcc tctacagcaa gctcaccgtg      960
gacaagagca ggtggcagca ggggaacgtc ttctcatgct ccgtgatgca tgaggctctg     1020
cacaaccact acacgcagaa gagcctctcc ctgtctccgg gtaaatgata gcggccgcgg     1080
atcccccgac ctcgacctct ggctaat                                         1107
```

<210> SEQ ID NO 11
<211> LENGTH: 355
<212> TYPE: PRT
<213> ORGANISM: Artificial Sequence
<220> FEATURE:
<223> OTHER INFORMATION: Synthetic Construct

<400> SEQUENCE: 11

```
Met Asp Ala Met Lys Arg Gly Leu Cys Cys Val Leu Leu Leu Cys Gly
1               5                   10                  15

Ala Val Phe Val Ser Asn Ser Glu Ser Asp Thr Arg Arg Lys Arg Met
            20                  25                  30

Trp Asn Ala Thr Pro Ser Glu Glu Pro Gly Phe Asn Leu Thr Leu Ala
        35                  40                  45

Asp Leu Asp Trp Asp Ala Ser Pro Gly Asn Asp Ser Leu Gly Asp Glu
    50                  55                  60

Leu Leu Gln Leu Phe Pro Ala Arg Leu Trp Gln Tyr Arg Pro Trp Asn
65                  70                  75                  80

Phe Gly Asp Leu Leu Cys Lys Leu Phe Gln Phe Val Ser Glu Ser Cys
                85                  90                  95

Thr Val Gly Val Glu His Glu Asn Gly Thr Asp Pro Trp Asp Thr Asn
            100                 105                 110

Glu Cys Arg Pro Thr Glu Phe Ala Val Arg Ser Gly Gly Gly Gly Ser
        115                 120                 125

Arg Lys Cys Cys Val Glu Cys Pro Pro Cys Pro Ala Pro Pro Val Ala
130                 135                 140

Gly Pro Ser Val Phe Leu Phe Pro Pro Lys Pro Lys Asp Pro Leu Met
145                 150                 155                 160

Ile Ser Arg Thr Pro Glu Val Thr Cys Val Val Val Asp Val Ser His
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Phe
        195                 200                 205

Arg Val Val Ser Val Leu Thr Val Val His Gln Asp Trp Leu Asn Gly
    210                 215                 220

Lys Glu Tyr Lys Cys Lys Val Ser Asn Lys Gly Leu Pro Ala Pro Ile
225                 230                 235                 240

Glu Lys Thr Ile Ser Lys Thr Lys Gly Gln Pro Arg Glu Pro Gln Val
                245                 250                 255

Tyr Thr Leu Pro Pro Ser Arg Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300
```

```
Met Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
            325                 330                 335

His Glu Ala Leu His Asn His Tyr Thr Gln Lys Ser Leu Ser Leu Ser
        340                 345                 350

Pro Gly Lys
        355

<210> SEQ ID NO 12
<211> LENGTH: 120
<212> TYPE: DNA
<213> ORGANISM: Homo Sapiens

<400> SEQUENCE: 12
atgtggaacg cgacgcccag cgaagagccg gggttcaacc tcacactggc cgacctggac      60
tgggatgctt cccccggcaa cgactcgctg ggcgacgagc tgctgcagct cttccccgcg     120

<210> SEQ ID NO 13
<211> LENGTH: 40
<212> TYPE: PRT
<213> ORGANISM: Homo Sapiens

<400> SEQUENCE: 13

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala
        35                  40

<210> SEQ ID NO 14
<211> LENGTH: 78
<212> TYPE: DNA
<213> ORGANISM: Homo Sapiens

<400> SEQUENCE: 14
cgcctctggc agtaccggcc ctggaacttc ggcgacctcc tctgcaaact cttccaattc      60
gtcagtgaga gctgcacc                                                    78

<210> SEQ ID NO 15
<211> LENGTH: 26
<212> TYPE: PRT
<213> ORGANISM: Homo Sapiens

<400> SEQUENCE: 15

Arg Leu Trp Gln Tyr Arg Pro Trp Asn Phe Gly Asp Leu Leu Cys Lys
1               5                   10                  15

Leu Phe Gln Phe Val Ser Glu Ser Cys Thr
            20                  25

<210> SEQ ID NO 16
<211> LENGTH: 78
<212> TYPE: DNA
<213> ORGANISM: Homo Sapiens

<400> SEQUENCE: 16
gtcggggtgg agcacgagaa cggcaccgac ccttgggaca ccaacgagtg ccgccccacc      60
gagtttgcgg tgcgctct                                                    78
```

<210> SEQ ID NO 17
<211> LENGTH: 26
<212> TYPE: PRT
<213> ORGANISM: Homo Sapiens

<400> SEQUENCE: 17

Val Gly Val Glu His Glu Asn Gly Thr Asp Pro Trp Asp Thr Asn Glu
1               5                   10                  15

Cys Arg Pro Thr Glu Phe Ala Val Arg Ser
            20                  25

<210> SEQ ID NO 18
<211> LENGTH: 1101
<212> TYPE: DNA
<213> ORGANISM: Homo Sapiens

<400> SEQUENCE: 18

| | | | | | |
|---|---|---|---|---|---|
| atgtggaacg | cgacgcccag | cgaagagccg | gggttcaacc | tcacactggc | cgacctggac | 60 |
| tgggatgctt | ccccggcaa | cgactcgctg | ggcgacgagc | tgctgcagct | cttccccgcg | 120 |
| ccgctgctgg | cgggcgtcac | agccacctgc | gtggcactct | tcgtggtggg | catcgctggc | 180 |
| aacctgctca | ccatgctggt | ggtgtcgcgc | ttccgcgagc | tgcgcaccac | caccaacctc | 240 |
| tacctgtcca | gcatggcctt | ctccgatctg | ctcatcttcc | tctgcatgcc | cctggacctc | 300 |
| gttcgcctct | ggcagtaccg | gcctggaac | ttcggcgacc | tcctctgcaa | actcttccaa | 360 |
| ttcgtcagtg | agagctgcac | ctacgccacg | gtgctcacca | tcacagcgct | gagcgtcgag | 420 |
| cgctacttcg | ccatctgctt | cccactccgg | gccaaggtgg | tggtcaccaa | ggggcgggtg | 480 |
| aagctggtca | tcttcgtcat | ctgggccgtg | gccttctgca | gcgccgggcc | catcttcgtg | 540 |
| ctagtcgggg | tggagcacga | aaccggcacc | gaccccttggg | acaccaacga | gtgccgcccc | 600 |
| accgagtttg | cggtgcgctc | tggactgctc | acggtcatgg | tgtgggtgtc | cagcatcttc | 660 |
| ttcttccttc | ctgtcttctg | tctcacggtc | ctctacagtc | tcatcggcag | gaagctgtgg | 720 |
| cggaggaggc | gcggcgatgc | tgtcgtgggt | gcctcgctca | gggaccagaa | ccacaagcaa | 780 |
| accgtgaaaa | tgctggctgt | agtggtgttt | gccttcatcc | tctgctggct | ccccttccac | 840 |
| gtagggcgat | atttattttc | caaatccttt | gagcctggct | ccttggagat | tgctcagatc | 900 |
| agccagtact | gcaacctcgt | gtcctttgtc | ctcttctacc | tcagtgctgc | catcaacccc | 960 |
| attctgtaca | acatcatgtc | caagaagtac | cgggtggcag | tgttcagact | tctgggattc | 1020 |
| gaacccttct | cccagagaaa | gctctccact | ctgaaagatg | aaagttctcg | ggcctggaca | 1080 |
| gaatctagta | ttaatacatg | a | | | | 1101 |

<210> SEQ ID NO 19
<211> LENGTH: 28
<212> TYPE: DNA
<213> ORGANISM: Mus Musculus

<400> SEQUENCE: 19
gcggggtacc atgtggaacg cgacgcca                                    28

<210> SEQ ID NO 20
<211> LENGTH: 33
<212> TYPE: DNA
<213> ORGANISM: Mus Musculus

<400> SEQUENCE: 20
gcgagtactc gcggggaaca gtggcagcag ttc                              33

<210> SEQ ID NO 21
<211> LENGTH: 63
<212> TYPE: DNA
<213> ORGANISM: Mus Musculus

<400> SEQUENCE: 21
gcgaagcttt tccagtttgt cagcgagagc tgcacctacg ccccagcga gaccgtcacc    60 tgc                                                                63

<210> SEQ ID NO 22
<211> LENGTH: 77
<212> TYPE: DNA
<213> ORGANISM: Mus Musculus

<400> SEQUENCE: 22
cgaagcttgc agagcaggtc gccgaagttc cagggccgat actgccagag gcgcgcgggg    60
aacagtggca gcagttc                                                  77

<210> SEQ ID NO 23
<211> LENGTH: 81
<212> TYPE: DNA
<213> ORGANISM: Mus Musculus

<400> SEQUENCE: 23
gcgacggatc cccgggacac caacgagtgc gcgccaccg agttcgctgt gcgctctccc     60
agcgagaccg tcacctgcaa c                                             81

<210> SEQ ID NO 24
<211> LENGTH: 66
<212> TYPE: DNA
<213> ORGANISM: Mus Musculus

<400> SEQUENCE: 24
gcggggatcc gtgccgttct cgtgctccac gcccaccagc acggcgtagg tgcagctctc    60
gctgac                                                              66

<210> SEQ ID NO 25
<211> LENGTH: 36
<212> TYPE: DNA
<213> ORGANISM: Mus Musculus

<400> SEQUENCE: 25
gcgagtactt ggcccagcga gaccgtcacc tgcaac                             36

<210> SEQ ID NO 26
<211> LENGTH: 34
<212> TYPE: DNA
<213> ORGANISM: Mus Musculus

<400> SEQUENCE: 26
gcgctcgagc agggaagaag tctgttatca tgca                               34

<210> SEQ ID NO 27
<211> LENGTH: 20
<212> TYPE: DNA
<213> ORGANISM: Mus Musculus

<400> SEQUENCE: 27
ccaaaaccct catcaagacc                                               20

```
<210> SEQ ID NO 28
<211> LENGTH: 20
<212> TYPE: DNA
<213> ORGANISM: Mus Musculus

<400> SEQUENCE: 28
tgtctccacc accgaaactc                                                   20

<210> SEQ ID NO 29
<211> LENGTH: 20
<212> TYPE: DNA
<213> ORGANISM: Homo Sapiens

<400> SEQUENCE: 29
tgtctccacc accgaaactc                                                   20

<210> SEQ ID NO 30
<211> LENGTH: 24
<212> TYPE: DNA
<213> ORGANISM: Homo Sapiens

<400> SEQUENCE: 30
tctccagttg aaccaagcag gtca                                              24

<210> SEQ ID NO 31
<211> LENGTH: 22
<212> TYPE: DNA
<213> ORGANISM: Homo Sapiens

<400> SEQUENCE: 31
ggaaagacaa cggacaaatc ac                                                22

<210> SEQ ID NO 32
<211> LENGTH: 20
<212> TYPE: DNA
<213> ORGANISM: Homo Sapiens

<400> SEQUENCE: 32
atccttggcc ctctgagatg                                                   20

<210> SEQ ID NO 33
<211> LENGTH: 21
<212> TYPE: DNA
<213> ORGANISM: Mus Musculus

<400> SEQUENCE: 33
tgtctgaagc agctatggca a                                                 21

<210> SEQ ID NO 34
<211> LENGTH: 20
<212> TYPE: DNA
<213> ORGANISM: Mus Musculus

<400> SEQUENCE: 34
tgctgcgaga tttgaagctg                                                   20

<210> SEQ ID NO 35
<211> LENGTH: 20
<212> TYPE: DNA
<213> ORGANISM: Mus Musculus

<400> SEQUENCE: 35
tgatcggtcc ccaaagggat                                                   20
```

```
<210> SEQ ID NO 36
<211> LENGTH: 19
<212> TYPE: DNA
<213> ORGANISM: Mus Musculus

<400> SEQUENCE: 36
ttgctacgac gtgggctac                                                   19
```